US006664258B1

(12) United States Patent
Fliri et al.

(10) Patent No.: US 6,664,258 B1
(45) Date of Patent: Dec. 16, 2003

(54) SPIROCYCLIC DOPAMINE RECEPTOR SUBTYPE LIGANDS

(75) Inventors: Anton F. J. Fliri, Stonington, CT (US); Todd W. Butler, Salem, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/242,819

(22) PCT Filed: Aug. 8, 1997

(86) PCT No.: PCT/IB97/00978

§ 371 (c)(1),
(2), (4) Date: Feb. 24, 1999

(87) PCT Pub. No.: WO98/08835

PCT Pub. Date: Mar. 5, 1998

Related U.S. Application Data

(60) Provisional application No. 60/024,797, filed on Aug. 26, 1996.

(51) Int. Cl.[7] ............... C07D 405/08; C07D 333/50; A61K 31/496
(52) U.S. Cl. .................. 514/252.13; 514/254.08; 514/254.11; 514/255.03; 544/230
(58) Field of Search ............. 544/230; 514/254.08, 514/254.11, 255.03, 252.13

(56) References Cited

U.S. PATENT DOCUMENTS

| 3,932,425 A | 1/1976 | Lednicer ............ 260/293.62 |
| 4,010,201 A | 3/1977 | Lednicer ............ 260/570.5 |
| 4,025,558 A | 5/1977 | Lednicer ............ 260/570.5 |
| 5,352,678 A | 10/1994 | Mattson et al. ............ 514/253 |
| 5,403,846 A | 4/1995 | Baldwin et al. ............ 514/278 |
| 5,614,524 A | 3/1997 | Matassa et al. ............ 514/253 |
| 5,631,269 A | 5/1997 | Broughton et al. ......... 514/326 |

FOREIGN PATENT DOCUMENTS

| DE | 1957490 | 6/1971 | ........ C07D/65/16 |
| DE | 2818329 | 11/1979 | ........ C07D/495/10 |
| WO | 9505940 | 3/1995 | ........ B32B/27/08 |
| WO | 9530642 | 11/1995 | ........ C07C/205/06 |

OTHER PUBLICATIONS

Van Tol et al.,Nature, vol. 350, p.610–614, 1991.*
TenBrink et al.,Journal of Medicinal Chemistry, vol. 39, p.2435–2437, 1996.*
Vassileva et al., Synthetic Communications, vol. 27(10), p.1669–1675, 1997.*
Martin, *J. Med. Chem.*, 24, 617–621, 1981.
Parham, *J. Org. Chem.*, 41, 2628–2633, 1976.

* cited by examiner

*Primary Examiner*—Emily Bernhardt
(74) *Attorney, Agent, or Firm*—P. C. Richardson; P. H. Ginsburg; A. D. Joran

(57) ABSTRACT

This invention relates to novel, pharmaceutically active compounds of formula (I) wherein a, b and $R^1$ through $R^6$ are as defined in the specification

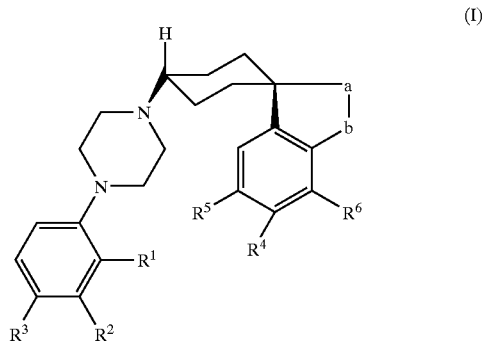

(I)

These compounds exhibit central dopaminergic activity and are useful in the treatment of CNS disorders.

8 Claims, No Drawings

SPIROCYCLIC DOPAMINE RECEPTOR SUBTYPE LIGANDS

This application is a 371 of PCT/IB97/00978 filed Aug. 8, 1997, which claims the benefit of U.S. Provisional Application No. 60/024,797 filed Aug. 26, 1996.

BACKGROUND TO THE INVENTION

The present invention pertains to novel pharmacologically active trans-piperazin-1-yl-spiro[cyclohexane-1,1'-isobenzofuran] derivatives that are dopamine receptor subtype ligands having a preference for the D4-dopamine receptor. These compounds exhibit central dopaminergic activity, as defined below, and are useful in the treatment and/or prevention of disorders of the dopamine system, including schizophrenic and schizoaffective disorders, akinesia, dementia, Parkinson's disease, nausea, bipolar disorders, emesis, tardive dyskinesia, extrapyramidal side effects from neuroleptic agents, neuroleptic malignant syndrome, hyperprolactemia and amenorrhoea.

The biological activity of only a few spirocyclic cylcohexane systems has been described. For example, in U.S. Pat. No. 3,932,425, U.S. Pat. No. 4,025,558 and U.S. Pat. No. 4,010,201, D. Lednicer refers to a series of spirocyclic cyclohexylamine derivatives that possess tranquilizing activity and are consequently useful in anxiety and schizophrenia and can be administered to reduce aggressive behavior and lower blood pressure. In U.S. Pat. No. 5,403,846, John J. Baldwin et al. refer to a series of spirocyclic benzopyrano cyclohexylamine derivatives that were studied for potassium channel blocking activity and found to exhibit type III antiarrythmic activity. In World Patent Application PCT/US95/05940, the same inventor, John J. Baldwin, refers to a series of spirocyclic dihydrobenzopyrano derivatives as constituting part of a combinatorial chemical library that contains ligands for potassium channels, adrenergic receptors, dopamine receptors and sigma-opioid receptors, and also refers to the use of this library for identifying biologically active agents such as, for example, inhibitors for carbonic acid anhydrase useful for treatment of glaucoma. Lawrence L. Martin describes, in J. Med. Chem., 24, pg. 617–621, 1981, the synthesis of a series of spiro isobenzofuran derivatives containing dialkylamino substituents and refers to the activity of these agents as centrally acting serotinergic agents. Similarly, William E. Parham describes, in J. Org. Chem., 41, pg. 2628–2633, 1976, the synthesis of a series of spiro[isobenzofuran-(3H),4'piperidine derivatives and biological activities that suggest their utility as antidepressant and antipsychotic agents. U.S. Pat. No. 5.352,678 refers to a series of dopaminergic cyclohexane derivatives and their use as antiischemic and antipsychotic agents.

U.S. Pat. No. 5,352,678, which issued on Oct. 4, 1994, refers to dopaminergic cyclohexane derivatives and to their utility as antiischemic and antipsychotic agents.

International Patent Application WO 94/19367, which was published on Sep. 1, 1994, refers to spiropiperidine derivatives and to their ability to increase endogenous hormone levels.

Thus, it is generally known that dopamine receptors are important for many functions in the animal body. For example, altered functions of these receptors are thought to participate in the genesis of psychosis, drug addiction, compulsive disorders, bipolar disorders, vision, emesis, sleep, feeding, learning, memory, sexual behavior, regulation of immunological responses and blood pressure. Since these receptors control a great number of pharmacological events and, on the other hand, not all of them are presently known, it is possible that compounds acting preferentially on dopamine receptor subtypes, for example, on the D4 dopamine receptor, will exert a wide range of therapeutic effects in humans.

SUMMARY OF THE INVENTION

This invention relates to compounds of the formula

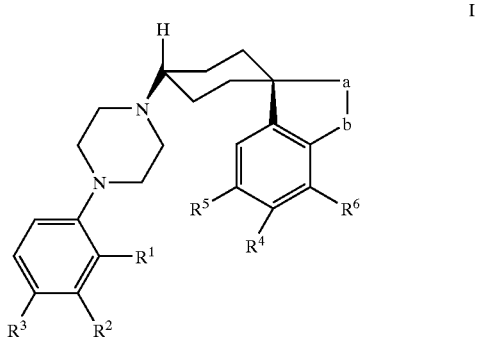

wherein a is oxygen, $CH_2$, $C(CH_3)_2$, $NR^{10}$, sulfur, SO or $SO_2$;

b is oxygen, $CH_2$, C=O, $C=NR^{11}$, C=NOH, $SO_2$, sulfur, SO, $C=NO(C_1-C_5)$alkyl or $CR^7R^8$;

each of $R^1$ through $R^8$ is selected, independently, from hydrogen, halogen (e.q., chloro, fluoro, bromo or iodo), trifluoromethyl, cyano and hydroxy, or $R^7$ and $R^8$ together can be $C(=O)NH_2$ or $C(=O)N(C_1-C_4)$alkyl, with the proviso that neither $R^7$ nor $R^8$ can be halo when a is oxygen, $NR^{11}$, sulfur, SO or $SO_2$; and each of $R^{10}$ and $R^{11}$ is selected, independently, from hydrogen, benzyl and $(C_1-C_6)$alkyl;

and the pharmaceutically acceptable salts of such compounds.

Preferred compounds of the formula I are those wherein a is oxygen, b is $CH_2$, each of $R^1$, $R^4$ and $R^5$ is hydrogen, and each of $R^2$, $R^3$ and $R^6$ is selected, independently from hydrogen, cyano, chloro and fluoro.

Other more specific embodiments of this invention include:

(a) compounds of the formula I wherein a is oxygen;

(b) compounds of the formula I wherein a is oxygen and b is $CH_2$;

(c) compounds of th formula I wherein a is oxygen, b is $CH_2$ and each of $R^1$, $R^4$ and $R^5$ is hydrogen;

(d) compounds of the formula I wherein a is oxygen, b is $CH_2$, each of $R^1$, $R^4$ and $R^5$ is hydrogen and $R^3$ is fluoro, cyano or chloro;

(e) compounds of the formula I wherein a is oxygen, b is $CH_2$, each of $R^1$, $R^4$ and $R^5$ is hydrogen and each of $R^2$, $R^3$ and $R^6$ is selected, independently, from hydrogen, fluoro, cyano and chloro; and (f) compounds of the formula I wherein a is oxygen, b is $CH_2$, each of $R^1$, $R^4$ and $R^5$ is hydrogen, and $R^2$ and $R^3$ are selected, independently, from fluoro, cyano and chloro.

The compounds of formula I above may contain chiral centers and therefore may exist in different enantiomeric forms. This invention relates to all optical isomers and all other stereoisomers of compounds of the formula I and mixtures thereof.

This invention also relates to a pharmaceutical composition for treating or preventing a condition selected from psychosis, affective psychosis, nonorganic psychosis, personality disorders, schizophrenic and schizoaffective disorders, bipolar disorders, dysphoric mania, Parkinson's disease, extrapyramidal side effects from neuroleptic agents, neuroleptic malignant syndrome, tardive dyskinesia, nausea, emesis, hyperthermia and amenorrhea in a mammal, including a human, comprising an amount of a compound of the formula I, or pharmaceutically acceptable salt thereof, that is effective in treating or preventing such condition, and a pharmaceutical acceptable carrier.

The present invention also relates to a method of treating or preventing a condition selected from psychosis, affective psychosis, nonorganic psychosis, personality disorders, schizophrenic and schizoaffective disorders, bipolar disorders, dysphoric mania, Parkinson's disease, extrapyramidal side effects from neuroleptic agents, neuroleptic malignant syndrome, tardive dyskinesia, nausea, emesis, hyperthermia and amenorrhea in a mammal, including a human, comprising administering to said mammal an amount of a compound of the formula I, or pharmaceutically acceptable salt thereof, that is effective in treating or preventing such condition.

The present invention also relates to a pharmaceutical composition for treating or preventing a condition selected from psychosis, affective psychosis, nonorganic psychosis, personality disorders, schizophrenic and schizoaffective disorders, bipolar disorders, dysphoric mania, Parkinson's disease, extrapyramidal side effects from neuroleptic agents, neuroleptic malignant syndrome, tardive dyskinesia, nausea, emesis, hyperthermia and amenorrhea in a mammal, including a human, comprising a dopaminergic effective amount of a compound of the formula I, or a pharmaceutical acceptable salt thereof, and a pharmaceutically acceptable carrier.

The present invention also relates to a method of treating or preventing a condition selected from psychosis, affective psychosis, nonorganic psychosis, personality disorders, schizophrenic and schizoaffective disorders, bipolar disorders, dysphoric mania, Parkinson's disease, extrapyramidal side effects from neuroleptic agents, neuroleptic malignant syndrome, tardive dyskinesia, and nausea, emesis, hyperthermia and amenorrhea in a mammal, including a human, comprising an administering to said mammal a dopaminergic effective amount of a compound of the formula I, or pharmaceutically acceptable salt thereof.

This invention also relates to a pharmaceutical composition for treating or preventing a disease or condition, the treatment or prevention of which can be effected or facilitated by altering (i.e., increasing or decreasing) dopamine mediated neurotransmission in a mammal, including a human, comprising a dopaminergic effective amount of a compound of the formula I, or a pharmaceutically acceptable salt thereof, and a pharmaceutically acceptable carrier.

This invention also relates to a method of treating or preventing a disease or condition, the treatment or prevention of which can be effected or facilitated by altering (i.e., increasing or decreasing) dopamine mediated neurotransmission in a mammal, including a human, comprising administering to said mammal a dopaminergic effective amount of a compound of the formula I, or a pharmaceutically acceptable salt thereof.

The present invention also relates to a pharmaceutical composition for treating or preventing a condition selected from psychosis, affective psychosis, nonorganic psychosis, personality disorders, schizophrenic and schizoaffective disorders, bipolar disorders, dysphoric mania, Parkinson's disease, extrapyramidal side effects from neuroleptic agents, neuroleptic malignant syndrome, tardive dyskinesia, nausea, emesis, hyperthermia and amenorrhea in a mammal, including a human, comprising a D4 receptor binding effective amount of a compound of the formula I, or a pharmaceutical acceptable salt thereof, and a pharmaceutically acceptable carrier.

The present invention also relates to a method of treating or preventing a condition selected from psychosis, affective psychosis, nonorganic psychosis, personality disorders, dysphoric mania, schizophrenic and schizoaffective disorders, bipolar disorders, Parkinson's disease, extrapyramidal side effects from neuroleptic agents, neuroleptic malignant syndrome, tardive dyskinesia, and nausea, emesis, hyperthermia and amenorrhea in a mammal, including a human, comprising an administering to said mammal a D4 receptor binding effective amount of a compound of the formula I, or pharmaceutically acceptable salt thereof.

The present invention also relates to a pharmaceutical composition for treating or preventing a condition selected from psychosis, affective psychosis, nonorganic psychosis, personality disorders, schizophrenic and schizoaffective disorders, bipolar disorders, dysphoric mania, Parkinson's disease, extrapyramidal side effects from neuroleptic agents, neuroleptic malignant syndrome, tardive dyskinesia, nausea, emesis, hyperthermia and amenorrhea in a mammal, including a human, comprising a D4 receptor binding effective amount of a compound of the formula I, or a pharmaceutical acceptable salt thereof, and a pharmaceutically acceptable carrier.

The term "dopaminergic effective amount", as used herein, refers to an amount of a compound sufficient to inhibit the binding of dopamine to a dopamine receptor with the effect of altering (i.e., increasing or decreasing) dopamine mediated neurotransmission.

The compounds of formula I that are basic in nature are capable of forming a wide variety of salts with various inorganic and organic acids. The acids that may be used to prepare pharmaceutically acceptable acid addition salts of those compounds of formula I that are basic in nature are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

This invention also relates to the pharmaceutically acceptable acid addition salts of compounds of the formula I.

The term "one or more substituents", as used herein, includes from one to the maximum number of substituents possible based on the number of available bonding sites.

The term "alkyl", as used herein, unless otherwise indicated, includes saturated monovalent hydrocarbon radicals having straight, branched or cyclic moieties or combinations thereof.

The term "alkoxy", as used herein, unless otherwise indicated, refers to radicals having the formula —O-alkyl, wherein "alkyl" is defined as above.

DETAILED DESCRIPTION OF THE INVENTION

Compounds of the formula I and their pharmaceutically acceptable salts may be prepared as described below. In the reaction scheme and discussion that follows, a, b, R[1] through R[11] and structural formula I are defined as above.
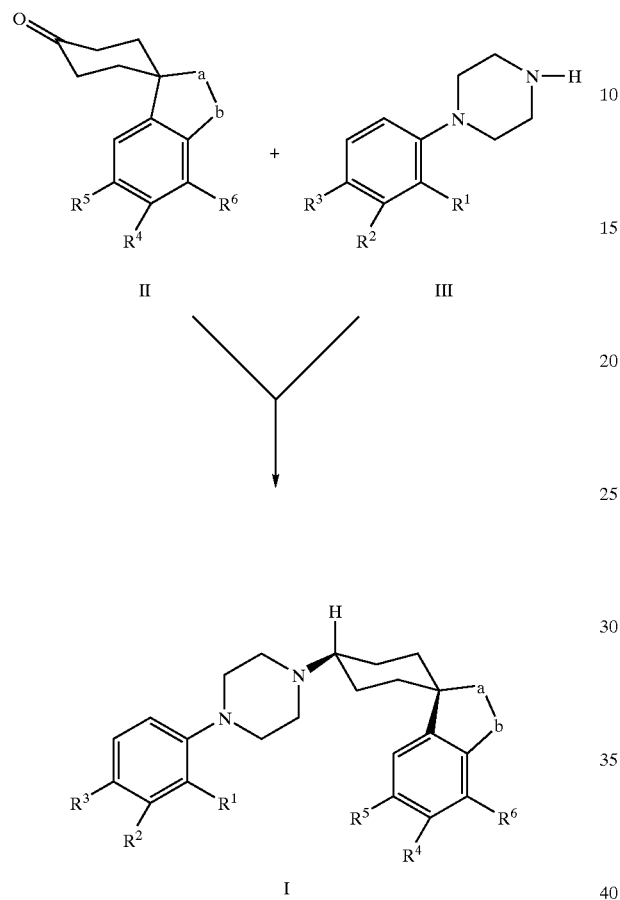
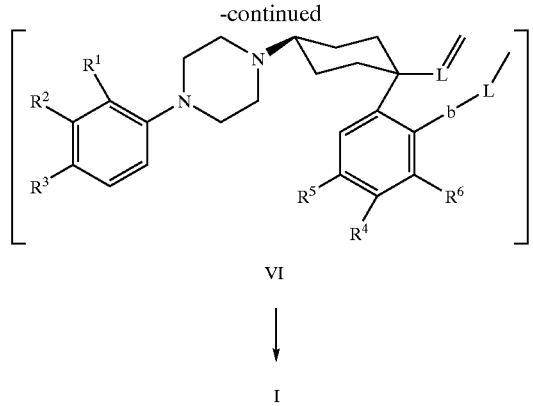
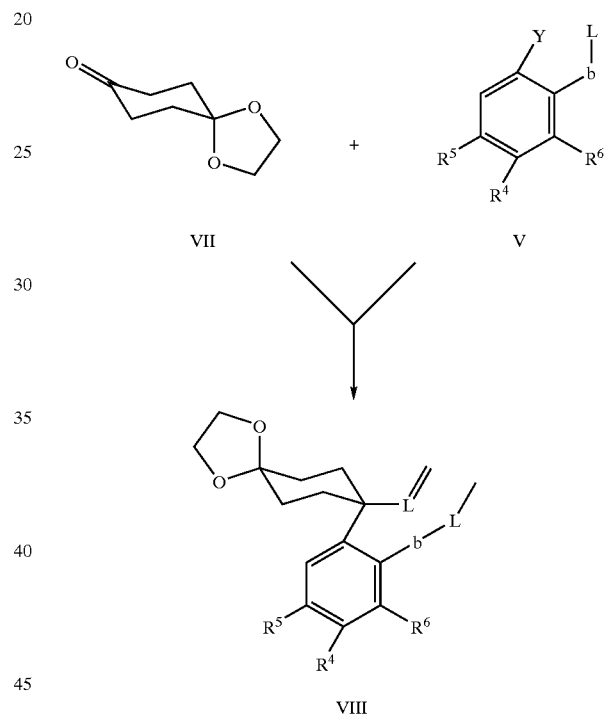
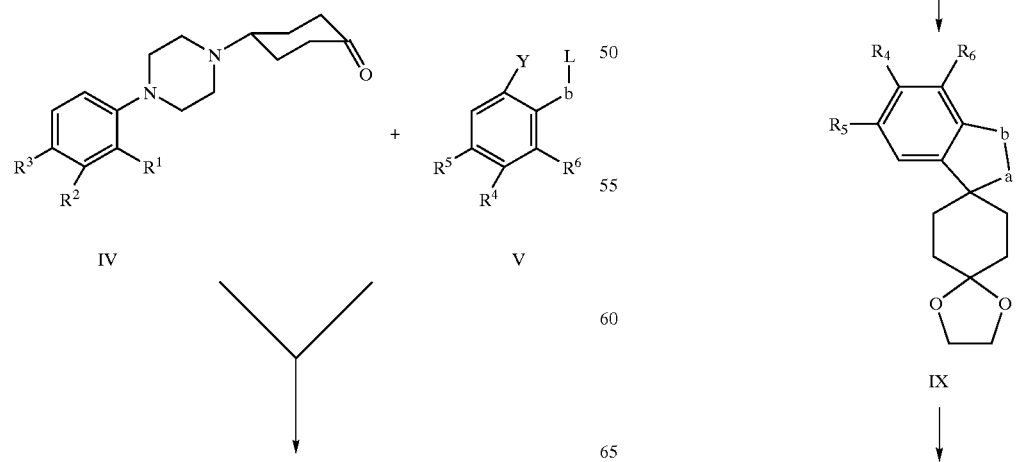

-continued
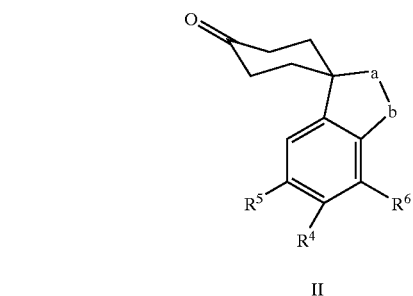
II
SCHEME 4
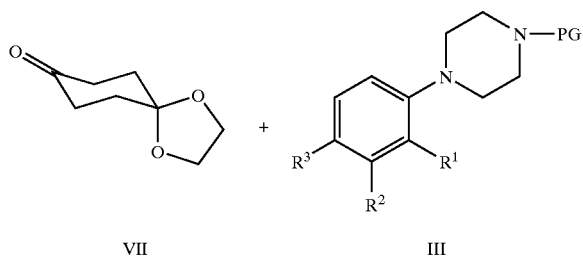
VII   III
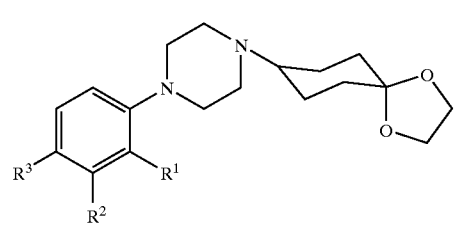
X
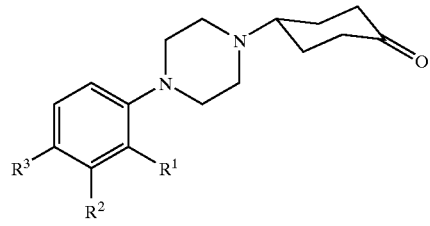
IV
SCHEME 5
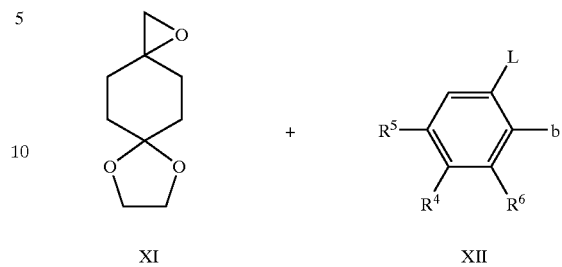
XI   XII
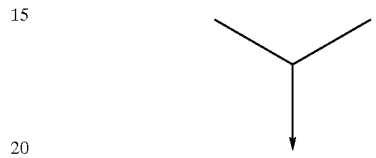
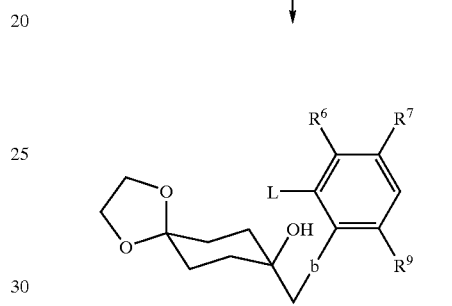
XIII
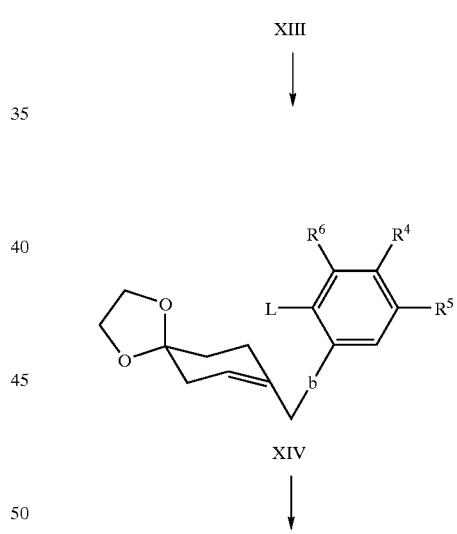
XIV
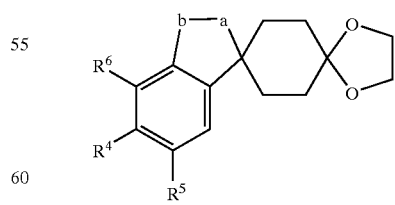
XV
II

SCHEME 6

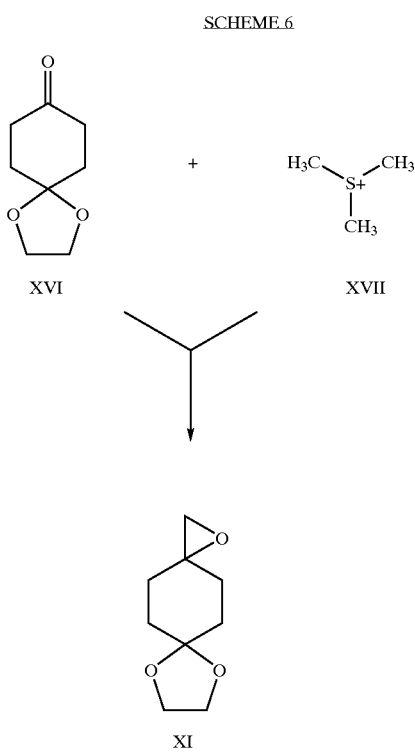

SCHEME 7

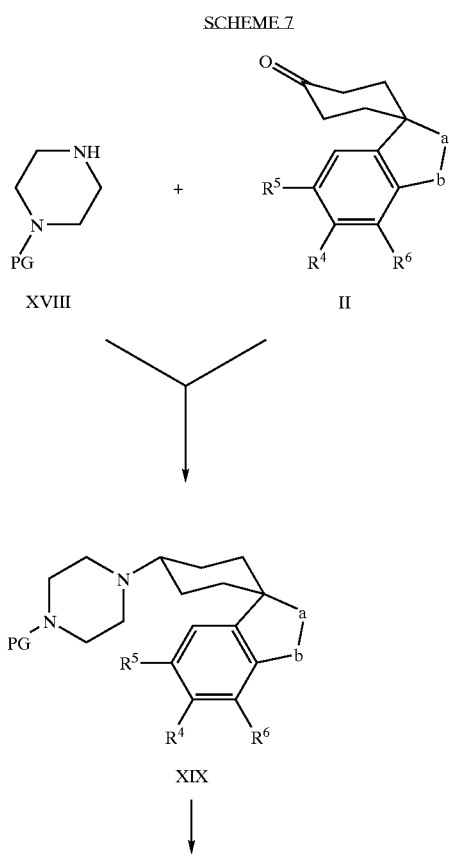

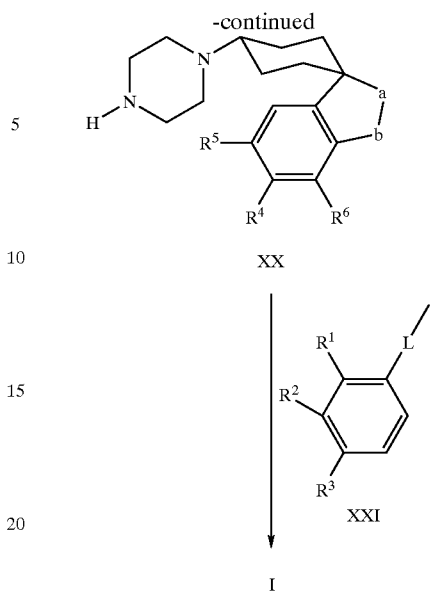

Schemes 1 and 2 illustrate methods of synthesizing compounds of the formula I.

Referring to scheme 1, a compound of the formula II is reacted with a compound of the formula III to form a compound of the formula I. This reaction is generally carried out in an inert solvent at a temperature from about 0° C. to about 150° C. preferably from about 0° C. to about the reflux temperature of the solvent. Suitable solvents include water, cyclic and acyclic mono and dialkylamides (e.q., N,N-dimethylformamide (DMF), N-methyl-2-pyrrolidinone (NMP), formamide and acetamide), ($C_1$–$C_4$)alkanols, halogenated hydrocarbon solvents (e.g., methylene chloride, chloroform and dichloroethane), acyclic and cyclic alkyl ethers (e.g., diisopropyl ether and tetrahydrofuran (THF)) and mixtures of two or more of the foregoing solvents.

Referring to scheme 2, a compound of the formula V, wherein Y is bromine, chlorine or iodine and L is a suitable group such as O-lithium, O-potassium, O-sodium, O-magnesium, —O—($C_1$–$C_4$)alkyl, N-Metal-phenyl wherein Metal is lithium, sodium, potassium or magnesium, —O-tri($C_1$–$C_4$)alkylsilyl or —NH-phenyl, is cooled to about −80° C. and converted into the corresponding compound wherein Y is lithium, potassium, sodium or magnesium, preferably lithium, using conventional methods (e.g., by addition of n-butyl lithium, t-butyl lithium or 2-methylpropyl lithium). After addition of the appropriate reagent, the reaction mixture is allowed to warm to room temperature. The resulting mixture containing the organometallic product of formula V is then cooled again to about −80° C. and a compound of the IV is added to it, as depicted in the scheme, to form an intermediate of the formula VI, wherein L' and LG" are the same or different and are selected from —OH, —O—$CH_2$—O—($C_1$–$C_4$)alkyl, —O-tri($C_1$–$C_4$)alkylsilyl, —$NH_2$, —NH-phenyl, —N—($C_1$–$C_4$)alkyl, —SH, —S-trityl and —N-benzyl. The intermediate of formula VI can be converted into the corresponding compound of formula I via a ring closure step, as described below. Both the formation of the organometallic compound of formula V and the reaction of such compound with a compound of the formula IV are typically carried out in inert organic solvents such as cyclic or acyclic alkyl ethers (e.g., diisopropyl ether or THF) or mixtures of two or more such solvents.

The intermediate of formula VI can either be isolated or converted in situ into the desired compound of formula I. If the reaction mixture containing the intermediate is quenched with water, the intermediate will not react further and will be able to be isolated from the mixture by conventional methods. If, however, the mixture is refluxed with hydrochloric acid or another strong acid (e.g., sulfuric acid, nitric acid or sulfurous acid) at a temperature from about 0° C. to about 150° C., preferably at the reflux temperature, and contains an inert solvent selected from cyclic and acyclic mono and dialkylamides, acyclic alkyl ketones, $(C_1-C_4)$alkanols and mixtures of two or more such solvents, ring closure will occur, producing a compound of the formula I.

Alternate ring closure methods that can be used to form compounds of the formula I from the corresponding intermediates of formula VI are referred to by Martin, L. L., *J. Med. Chem.*, 24, 617–621 (1981). This article is incorporated herein by reference in its entirety.

Scheme 3 illustrates a method of preparing the starting materials of formula II that are used in scheme 1. This method involves reacting the compound having formula VII with an organometallic compound of the formula V wherein Y is lithium, potassium, sodium or magnesium, preferably lithium. This reaction is typically carried out in a similar manner (and using similar solvents and conditions) to the reaction depicted in scheme 2 which forms the intermediate of formula VI. Thus, a compound of the formula V, wherein Y is chloro, bromo or iodo and L is defined as above, is cooled to a temperature of about −80° C. and converted, using conventional techniques, into the corresponding compound wherein Y is lithium, potassium, sodium or magnesium, preferably lithium, and then allowed to warm to room temperature. The reaction mixture containing the organometallic product of formula V is then cooled again to about −80° C. and a compound having formula VII is added to it to form an intermediate of the formula VIII, after which the mixture is again allowed to warm to about room temperature. As was the case for the process depicted in scheme 2, quenching the reacting mixture with water will prevent further reaction of the intermediate and allow it to be isolated, while refluxing with a strong acid will cause closure of the a-b-containing spirocyclic ring and hydrolytic removal of the ketal group to form the desired compound of formula II.

Compounds of the formula II wherein a is oxygen and b is oxygen or $CH_2$ can be formed from the corresponding compounds of the formula VIII wherein L' and L" are hydroxy by treating the latter compound with a mineral acid (e.g., hydrochloric acid, phosphoric acid, sulfuric acid, perchloric acid, or nitric acid) in a mixture containing an inert solvent selected from cyclic and acyclic mono and dialkylamides, cyclic and acyclic mono and dialkylethers, acyclic alkyl ketones, $(C_1-C_4)$alkanols and mixtures of two or more such solvents. The reaction temperature can range from about 0° C. to about 150° C., and is preferably about the reflux temperature of the reaction mixture.

The spirocyclic ring of compounds of the formula II can be formed, alternatively, by reacting a compound of the formula VIII, wherein b is $CH_2$ and L' is hydrogen, with N-bromo, N-chloro or N-iodo succinimide in the presence of a radical generating agent (e.g., dibenzoyl peroxide or ultraviolet light). The corresponding compound of formula II is then formed by removing the ketal protecting group in intermediary products under acidic conditions.

The spirocyclic ring of compounds of the formula II wherein b is $CH_2$ or oxygen and a is NH, $N(C_1-C_4)$alkyl or S can be formed, alternatively, from compounds of the formula VIII wherein b is $CH_2$ or oxygen and L' and L" are selected, independently, from O-sulfonyl, —$(C_1-C_5)$alkyl, —O-sulfonylphenyl, halo and like substituents, by treating the latter compounds with the appropriate lower alkylamine, ammonia, benzylamine or sodium sulfide. This reaction is generally carried out in an inert organic solvent selected from cyclic and acyclic mono and dialkylamides, cyclic and acyclic mono and dialkylethers, cyclic and acyclic alkylketones, $(C_1-C_4)$alkanols and mixtures containing two or more such solvents, at a temperature from about 0° C. to about 150° C., preferably at the reflux temperature.

Another process for the preparation of compounds of formula II wherein b is $CH_2$ is illustrated in schemes 5 and 6 and described below. Starting with compounds of the formula XIII

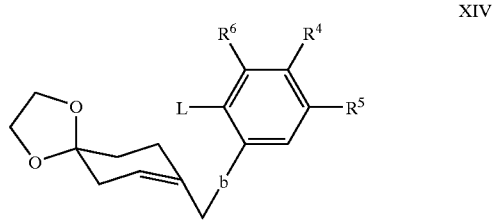

XIV such compounds can be converted into compounds of the formula II in the presence of a trialkyltin-hydride such as, for example, tributyltinhydride and a radical generating reagent such as, for example, azo-bis-(isobutyronitrile) and by removing the ketal protecting group in the intermediary products under acidic conditions. This conversion can be carried out in a solvent such as benzene or toluene at a temperature ranging from about 25° C. to about the reflux temperature. When protecting groups such as, for example, acetals are used, it may be convenient to remove such groups under acidic procedures. Similarly, other commonly used protecting groups may be introduced and removed using methods generally known to those skilled in the art.

Compounds of formula XIV may be prepared from the corresponding compounds having the general structure XIII

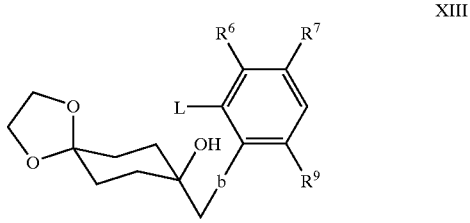

XIII

The conversion of compounds having the general structure XIII into compounds of the formula XIV can be conveniently carried out in an inert organic solvent such as methylene chloride or chloroform, at temperature ranging from about −25° C. to about the reflux temperature, in the presence of an $(C_1-C_4)$alkyl-sulfonylchloride and an acid acceptor such as an alkali carbonate, a tertiary amine or a similar reagent.

Intermediates of the formula XIII wherein, for example, b is oxygen, sulfur or amino, may be prepared by reacting compounds of the formula XII

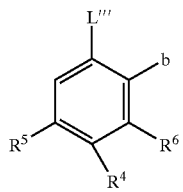

XII wherein L''' is bromo and b is hydroxy, mercapto or amino with a compound of the formula XI

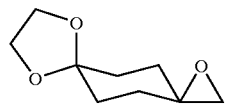

XI

This reaction can be conveniently carried out in an inert organic solvent such as benzene, toluene, xylene, pyridine, collidine, methylene chloride or chloroform, at a temperature ranging from about 25° C. to about the reflux temperature of the reaction mixture, in the presence of an acid acceptor such as an alkali carbonate, a tertiary amine or a similar reagent.

Compounds having the general formula XII are either commercially available or known in the literature. Compounds of the formula XI can be prepared from commercially available cyclohexanone derivatives and trialkylsulfonium derivatives using known methods such as those described by Rene Gree, *Synthetic Communication*, 15(8), 749–757 (1985).

Compounds of the formula V can be prepared from commercially available materials by known methods, e.g., as described by L. L. Martin in *J. Med. Chem.*, 24, 617–621, 1981, referred to above. This reference is incorporated herein by reference in its entirety.

Scheme 4 illustrates the preparation of compounds of the formula IV, which are used as starting materials in the process depicted in scheme 2. Referring to scheme 4, a compound of the formula VII is first reacted with a compound of the formula III to form a compound of the formula X. This reaction is generally carried out using the same solvents and conditions described above for the reaction depicted in scheme 1 (i.e., the formation of compounds of the formula I from the reaction of compounds of the formulae II and III). Thus, compounds embraced in general formula X may be prepared by reacting compounds having the general formula III with the cyclohexanone derivative of formula VII in a solvent selected from water, cyclic and acyclic mono and dialkylamides, ($C_1$–$C_4$)alkanols, halogenated solvents, acyclic and cyclic alkylethers and mixtures of two or more such solvents at temperatures ranging from 0° C. to about 150° C. preferably from about 0° C. to about the reflux temperature of the reaction mixture.

Compounds of the general formula IV may be prepared by hydrolysing compounds with general formula X with an aqueous mineral acid in a solvent selected from cyclic and acyclic mono and dialkylamides, cyclic and acyclic mono and dialkylethers, cyclic and acyclic alkylketones, ($C_1$–$C_4$) alkanols and mixtures of two or more such solvents at temperatures ranging from about 0° C. to about 150° C., preferable at the reflux temperature of the mixture.

Compounds with general formula III may be prepared by reacting piperazine derivatives with an appropriate aryl transferring group in a solvent selected from cyclic and acyclic mono and dialkylamides, ($C_1$–$C_4$)alkanols, cyclic and acyclic alkylethers, cyclic and acyclic alkylesters, cyclic and acyclic alkylketones, pyridine derivatives, halogenated solvents and mixtures of two or more such solvents at temperatures ranging from about 0° C. to about 150° C., preferably from about 0° C. to about the reflux temperature of the mixture. Addition of acid acceptors such as an alkali carbonates, tertiary amines or similar reagents as well as the addition of dehydrating reagents may be useful.

An alternate method of preparing compound of the formula I is illustrated in Scheme 7.

Referring to Scheme 7, a compound of formula XIX may be prepared by reacting a compound of formula XVIII, wherein PG is a nitrogen protecting group, with compound of the formula II, in water or an inert organic solvent such as those selected from polychlorinated $C_1$–$C_2$ alkanes, cyclic and acyclic mono and dialkylamides (e.g., N,N-dimethylformamide (DMF), N-methyl-2-pyrrolidinone (NMP), formamide and acetamide), ($C_1$–$C_4$)alkanols, halogenated hydrocarbon solvents (e.g., methylene chloride, chloroform and dichloroethane), acyclic and cyclic alkyl ethers (e.g., diisopropyl ether and tetrahydrofuran (THF)) and mixtures of two or more of the foregoing solvents, at temperatures ranging from about 0° C. to about 150° C., preferably at 0° C. or the boiling point of the solvent mixture.

Compounds of formula XX can then be prepared by deprotecting a compound of general formula XIX according to a method suitable to the protecting group selected. For example, when the protecting group is benzyl, trityl, benzhydryl or carbobenzyloxy, deprotection may be accomplished by hydrogenation in presence of a catalyst, in a solvent in selected from water and inert organic solvents, such as those selected from cyclic and acyclic mono and dialkylamides, ($C_1$–$C_4$) alcohols, acyclic and cyclic alkylethers and mixtures of two or more of the foregoing solvents, at temperatures ranging from about 0° C. to about 150° C. When the protecting group is tertiarybutoxycarbonyl or benzyloxycarbonyl, deprotection may be accomplished by treating a compound of formula XIX with an acid in water or an inert organic solvent such as those selected from cyclic and acyclic mono and dialkylamides, ($C_1$–$C_4$) alcohols, acyclic and cyclic alkylethers, and mixtures of two or more of the foregoing solvents, at temperatures ranging from about 0° C. to about 150° C.

Compounds of general formula I can be prepared by reacting a compound of the formula XX with an appropriate aryl transferring group in water or an inert organic solvent, such as those selected from cyclic and acyclic mono and dialkylamides, $C_1$–$C_4$ alcohols, cyclic and acyclic alkylethers, cyclic an acyclic alkylesters, cyclic and acyclic alkyletones, pyridine derivatives, halogenated hydrocarbons, and mixtures of two or more of the foregoing solvents, at temperatures ranging from about 0° C. to 150° C., preferable from about 0° C. or the to the reflux temperature of the solvent mixture. addition of acid acceptors such as an alkali carbonates, tertiary amines or similar reagents as well as the addition of dehydrating reagents may be useful.

Compounds embraced in general formula III are either commercially available or can be prepared by reacting known piperazine derivatives with aryl transferring reagents. Thus, these reactions can be conveniently carried out in water or an inert organic solvent such as those selected from alcohols, pyridine, cyclic and acyclic alkylketones, cyclic and acyclic alkylesters, cyclic and acyclic alkylethers, cyclic and acyclic mono and dialkylamides, and mixtures of two or more of the foregoing solvents, at temperatures ranging from −80° C. to 150° C. Addition of acid acceptors such as an alkali carbonates, tertiary amines or similar reagents, as well as the addition of dehydrating reagents, may be useful.

The reaction of arylmetal compounds with cyclohexanone derivatives is preferably performed at a temperature from about −80° C. to about 0° C. All other reaction steps are preferable carried out at temperatures ranging from about 0° C. to about the reflux temperature of the solvent. When ketone protecting groups such as acetals are employed, it may be convenient to remove these groups using acidic reaction conditions. Similarly, other commonly used protecting groups may be introduced and removed according to methods generally known to someone skilled in the art.

The preparation of other compounds of the formula I not specifically described in the foregoing discussion section can be accomplished using combinations of the reactions described above that will be apparent to those skilled in the art.

In each of the reactions discussed or illustrated in schemes 1 to 7 above, pressure is not critical unless otherwise indicated. Pressures from about 0.5 atmospheres to about 4 atmospheres are generally acceptable, and ambient pressure, i.e., about 1 atmosphere, is preferred as a matter of convenience.

The novel compounds of the formula I and their pharmaceutically acceptable salts (hereinafter "the therapeutic compounds of this invention") are useful as dopaminergic agents, i.e., they possess the ability to alter dopamine mediated neurotransmission in mammals, including humans. They are therefore able to function as therapeutic agents in the treatment of a variety of conditions in mammals, the treatment or prevention of which can be effected or facilitated by an increase or decrease in dopamine mediated neurotransmission. Such conditions include psychosis, affective psychosis, nonorganic psychosis, personality disorders, schizophrenic and schizoaffective disorders, bipolar disorders, dysphoric mania, emesis, nausea, Parkinson's disease, extrapyramidal side effects from neuroleptic agents, neuroleptic malignant syndrome, tardive dyskinesia, hyperdermia and amenorrhea.

The compounds of the formula I that are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

The therapeutic compounds of this invention can be administered orally, transdermally (e.g., through the use of a patch), parenterally or topically. Oral administration is preferred. In general, these compounds are most desirably administered in dosages ranging from about 0.01 mg up to about 250 mg per day, although variations may occur depending on the weight and condition of the person being treated and the particular route of administration chosen. In some instances, dosage levels below the lower limit of the aforesaid range may be more than adequate, while in other cases still larger doses may be employed without causing any harmful side effect, provided that such larger doses are first divided into several small doses for administration throughout the day.

The therapeutic compounds of the invention may be administered alone or in combination with pharmaceutically acceptable carriers or diluents by either of the two routes previously indicated, and such administration may be carried out in single or multiple doses. More particularly, the novel therapeutic compounds of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Such carriers include solid diluents or fillers, sterile aqueous media and various non-toxic organic solvents. etc. Moreover, oral pharmaceutical compositions can be suitably sweetened and/or flavored.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well known to those skilled in the art.

Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The D4 dopaminergic activity of the compounds of the present invention may be determined by the following procedure.

The determination of D4 dopaminergic activity has been described by Van Tol et al., *Nature*, vol. 350, 610 (London, 1991). Clonal cell lines expressing the human dopamine D4 receptor are harvested and homogenized (teflon pestle) in a 50 mM Tris.HCl (pH 7.4 at 4° C.) buffer containing 5 mM EDTA, 1.5 mM calcium chloride ($CaCl_2$), 5 mM magnesium chloride ($MgCl_2$), 5 mM potassium chloride (KCl) and 120 mM sodium chloride (NaCl). The homogenates are centrifugated for 15 min. at 39,000 g, and the resulting pellets resuspended in a buffer at a concentration of 150–250 µg/ml. For saturation experiments, 0.25 ml aliquots of tissue homogenate are incubated in duplicate with increasing concentrations of [$^3$H]Spiperone (70.3 Ci/mmol; 10–3000 pM final concentration) for 30–120 minutes at 22° C. in a total volume of 1 ml. For competition binding experiments, assays are initiated by the addition of 0.25 ml of membrane and incubated in duplicate with the indicated concentrations of competing ligands ($10^{-14}$–$10^{-13}$ M) and [$^3$H]Spiperone (100–300 pM) in either the absence or presence of 200 uM GPP(NH)$^p$ (5'/guanylylimidodiphosphate), where indicated, for 60–120 min at 22° C. Assays are terminated by rapid filtration through a Titertek cell harvester and the filters subsequently monitored for tritium as described by Sunahara, R. K. et al., *Nature*, 346, 76–80 (1990). For all experiments, specific [$^3$H]Spiperone binding is defined as that inhibited by 1–10 µM (+) Butaclamole or 1 µM Spiperone. Both saturation and competition binding data are analyzed by the non-linear least square curve-fitting program Ligand run on a digital Micro-PP-11 as described by Sunahara et. al.

The present invention is illustrated by the following Examples. It will be understood, however, that the invention is not limited to the specific details of the Examples.

EXAMPLE 1 trans, Piperazine, 1-[4-Fluorophenyl)-4-spiro [benzofuran-3(2H),1'-cyclohexan]-4'-yl), Hydrochloride 0.130 g (0.643 mmol, 1.0 equiv.) of 3'H-Spiro [cyclohexane-1,1'-isobenzofuran]-4-one was added to 4 ml 1,2 dichloroethane. 0.127 g (0.707 mmol, 1.1 equivalents (equiv.) 4-fluorophenyl piperazine was then added along with 2.0 equiv. (0.2739) sodium triacetoxyborohydride. The mixture was stirred at room temperature for 12 hours. To this mixture was added 2N sodium hydroxide (NaOH) 1 ml and the mixture was stirred for 1 hour and then extracted with ethyl acetate. The residue obtained after removal of solvents was purified via Flash Chrom.: stationary phase $SiO_2$, eluent 10% EtOAc/hexane. Fractions containing the cis and trans isomers, were collected. The residues obtained after removal of solvents were dissolved in ethanol (EtOH) and treated with a saturated solution of hydrochloric acid (HCl) in EtOH. The white precipitates obtained were filtered and dried under vacuum. Rf$^1$ is the isomer carrying the phenyl group and piperazine group in equatorial/axial positions (hereinafter denoted as trans).

$C_{23}H_{27}N_2O$, FW=366.48 (FREEBASE), 402.93 (HCl salt). GC-MS 10.33 Min., M$^+$ 366. MP>250° C. (HCl). $^1$H NMR (250 MHz, $CDCl_3$) δ 1.5–1.8 (2H, br m), 1.6–2.0 (6H, br m), 2.45 (1H, m), 2.7 (4H, m), 3.1 (4H, m), 6.8–7.4 (8H, aromatic). $^{13}$C NMR (63 MHz, $CDCl_3$) δ 24.93, 34.17, 45.11, 49.55, 50.53, 61.11, 83.34, 109.91, 115.29, 115.64, 117.63, 117.75, 120.16, 124.60, 128.19, 135.06, 148.01, 159.87.

EXAMPLE 2 trans, 2-Fluoro-4-(4-3'H-spiro[cyclohex-1,1'-isobenzofuran]-4-yl-piperazin-1-yl)-benzonitrile 0.493 g, 2.4 mmol of 3'H-Spiro[cyclohexane-1,1'-isobenzofuran]-4-one was added to 6.0 ml 1,2 dichloroethane and 1.0 equiv. of 1(4-cyano-3-fluorophenyl) piperazine (0.5 g, 2.43 mmol). Sodium triacetoxyborohydried 2.0 equiv. (1.03 g, 4.87 mmol) was added last. Contents of the flask were stirred at room temperature for 18 hours and poured into water ($H_2O$) and extracted with methylene chloride ($CH_2Cl_2$). The organic layer was dried with magnesium sulfate ($MgSO_4$) and concentrated down, leaving a solid. [On a small scale (<3 grams) the product is dried and the cis/trans isomers purified by flash chromatography. On larger scale, the products will precipitate on a flash column using EtOAc/hexane]. The mixture of cis/trans isomers were added to a large flask containing EtOH. The EtOH was refluxed until the compounds are solubilized. Upon cooling, one of the isomers began to precipitate from the EtOH before the other isomer. This procedure was repeated to further purify the isomers. The isomer with the highest Rf value (least polar) was trans 2-fluoro-4-(4-3'H-spiro [cyclohex-1,1'-isobenzofuran]-4-yl-piperazin-1-yl)-benzonitrile.

$C_{24}H_{27}FClN_3O$, (HCl), $C_{25}H_{30}FN_3O_4S$ (mesylate). FW=391.49 (freebase), 427.95 (HCl), 487.60 (mesylate). mp: Freebase 198° C., HCl>250° C., mesylate=263° C. (decomposition) GC-MS 10.72 Min., M+391. $^1$H NMR ($CDCl_3$ 400 MHz) δ 1.6 (m, 2H), 1.9 (m, 4H), 2.0 (m, 2H), 2.4 (s, 1H), 2.69 (m, 4H), 3.37 (m, 4H), 5.0 (s, 2H), 6.63 (m, 2H), 7.2 (m, 4H), 7.4 (m, 1H). $^{13}$C NMR ($CDCl_3$ 100 MHz) δ 24.7, 33.0, 47.3, 49.4, 58.9, 70.5, 86.7, 100.4, 100.6, 109.7, 115.4, 121.1, 121.2, 127.1, 127.4, 133.9, 139.2, 146.2, 155.2, 155.3, 166.1. Analysis calculated for $C_{24}H_{26}FN_3O$ HCl: C, 67.36; N, 9.82. Found: C, 67.04; H, 6.48; N, 9.94.

EXAMPLE 3 trans, Spiro[(cyclohex-1,3'-isoindolin)-1'-one]4-yl-4-(4-fluoro-phenyl)-piperazine Dihydrochloride 1-(4-Fluorophenyl)piperazine (0.75 g, 4.14 mmol), sodium triacetoxyborohydride (1.76 g, 8.30 mmol), and Spiro[cyclohexane-1,1'-[1H]isoindole]-3',4(2'H)-dione (0.90 g, 4.18 mmol) were dissolved in 1,2-dichloroethane (100 mL) and stirred overnight at ambient temperature. The reaction was concentrated and stirred with 1N NaOH and ethyl acetate (50 mL each) for 1 hour. The organic phase was washed with brine, dried over magnesium sulfate and concentrated onto silica gel. Flash column chromatography on silica gel (1.5"×4") was performed. The column was flushed with 2500 mL 50% ethyl acetate/hexane and the trans diastereomer was removed using 750 mL 75% ethyl acetate/hexane as eluent. Concentration gave a white solid (0.317 g), which was further purified by recrystallization from ethyl acetate/methylene chloride to yield 0.135 g (9%). The hydrochloride salt was prepared in absolute ethanol with HCl gas to give a white solid, trans-, spiro[(cyclohex-1,3'-isoindolin)-1'-one]-4-yl-4-(4-fluoro-phenyl)-piperazine. mp=238.5–242° C. Analysis calculated for $C_{23}H_{26}FN_3O.2HCl.2.5H_2O$: C, 55.54; H, 6.28; N, 8.44. Found: C, 55.49; H, 6.15; N, 8.24.

EXAMPLE 4 trans-1-(3',3'-Dimethyl-3'H-spiro[cyclohex-1,1'-isobenzofuran]-4-yl)-4-(4-fluoro-phenyl)-piperazine Dihydrochloride 3',3'-dimethyl-3'H-spiro[cyclohexane-1,1'-isobenzofuran]-4-one (0.95 g, 3.46 mmol). 1-(4-fluorophenyl)piperazine (0.63 g, 3.50 mmol) and sodium triacetoxyborohydride (1.48 g, 6.98 mmol) were stirred in 1,2-dichloroethane overnight. The reaction was concentrated and the residue stirred 1 hour with 75 mL each ethyl acetate and 1N sodium hydroxide. The organic phase was washed with water and brine, dried over magnesium sulfate and concentrated onto silica gel. The products were separated by flash chromatography on silica gel (1.5"×4"). Elution with 25% ethyl acetate/hexane (500 mL) gave the trans diastereomer of 1-(3',3'-dimethyl-3'H-spiro[cyclohex-1,1'-isobenzofuran]-4-yl)-4-(4-fluoro-phenyl)-piperazine as a white solid (0.32 g, 23%), which was converted to the dihydrochloride salt in ethanol with HCl gas.

mp>260° C. Analysis calculated for $C_{25}H_{31}FN_2O.2HCl.0.25H_2O$: C, 63.62; H, 7.15; N, 5.94. Found: C, 63.50; H, 6.92; N, 5.59.

Examples for the Preparation of Intermediates With General Structure II

EXAMPLE 5

3'H-Spiro[cyclohexane-1,1'-isobenzofuran]-4-one 0.64 g (2.62 mmol) of 8-(2-Hydroxymethyl-phenyl)-1,4-dioxa-spiro[4.5]decan-8-ol was added to 80% trifluoroacetate (TFA) 2.5 ml. The mixture was stirred at room temperature for 5 hours. Rotory evaporation of the TFA left thick brown oil. The oil was dissolved in 2.0 ml of EtOAc and washed first with 1N NaOH and then with $H_2O$. The organic layer was dried with $MgSO_4$ and concentrated, leaving a thick yellow oil. Hexane/ether (2:1) was added and the sides of the flask were scratched. A precipitate began to form. 0.23 Grams of 3'H-Spiro[cyclohexane-1,1'-isobenzofuran]-4-one were obtained, 44% yield.

1H NMR ($CDCl_3$, 400 MHz) δ 2.16–2.11 (m, 4H), 2.41–2.35 (m, 2H), 2.95–2.83 (m, 2H), 5.16 (s, 2H), 7.11–7.08 (m, 1H), 7.33–7.23 (m, 3H). $^{13}C$ NMR ($CDCl_3$, 100 MHz) δ 36.98, 37.92, 71.14, 85.14, 120.5, 121.31, 127.52, 127.97, 138.8, 144.37, 211.55. Analysis calculated for $C_{24}H_{26}FN_3O$ HCl: C, 77.20; H, 6.98. Found: C, 77.21; H, 7.06.

EXAMPLE 6

8-[2-(1-Hydroxy-1-methyl-ethyl)-phenyl]-1,4-dioxa-spiro[4.5]deca-8-ol (1.37 g, 4.69 mmol) and boron trifluoride diethyl etherate (1.2 mL, 9.76 mmol, 2 equiv.) were stirred overnight at ambient temperature in benzene (75 mL). Water (25 mL) was added and the reaction was stirred for 45 min. The organic phase was washed with saturated sodium bicarbonate and brine, and then dried over magnesium sulfate and concentrated to a waxy yellow solid (1.13 g). This material was partially purified by flash chromatography (1.5"×4" silica gel, 250 mL 10% ethyl acetate/hexane) to yield 0.95 g (88%) of 3',3'-dimethyl-3'H-spiro[cyclohexane-1,1'-isobenzofuran]-4-one as a light yellow solid, which was used in the next reaction without further purification.

EXAMPLE 7

Spiro[cyclohexane-1,1'-benzofuran]-4-one

The ketal protecting group of 3'H-spiro[cyclohexane-1,1'-benzofuran]-4-one diethylacetal, was removed by dissolving it in 5 ml dioxane, adding 2 ml 1 N HCl and refluxing the mixture for four hours. The mixture was concentrated to dryness, EtOAc was added, the mixture was washed with water, and the organic layer was dried with sodium sulfate. The residual white solid, 0.130 g, consisted of 3'H-spiro[cyclohexane-1,1'-benzofuran]-4-one.

GC-MS FW=202.25. 1 peak at 3.770 min. $^1H$ NMR (250 MHz, $CDCl_3$) δ 2.12–2.19 (4H, m), 2.49–2.57 (4H, m), 4.56 (2H, s), 6.8–7.2 (4H, aromatic). $^{13}C$ NMR (63 MHz, $CDCl_3$) δ 159.26, 133.37, 128.81, 122.75, 120.80, 110.04, 80.11. 45.23, 38.29, 36.18.

EXAMPLE 8

Spiro[cyclohexane-1,1'-[1H]isoindole]-3',4(2'H)-dione

Crude Spiro-[(cyclohexan-1,3'-isoindolin)-1'-one]-one (1.3 g, 5.0 mmol) was added to ice cold perchloric acid (30 mL) and stirred for 2 hours. The reaction was made basic by careful addition of sodium hydroxide pellets (added slowly to keep the temperature low). The basic mixture was extracted with ethyl acetate (3×60 mL) and the combined extracts were washed with water and brine, dried over $MgSO_4$ and concentrated onto silica gel. Purification by silica gel flash chromatography using 50% ethyl acetate/hexane gave (0.95 g, 88%) of the desired spirocyclohexanone-benzolactam product, spiro[cyclohexane-1,1'-[1H]isoindole]-3',4(2'H)-dione, as a foamy white solid.

Mp 55–65° C. $^1H$ NMR DMSO $d_6$ 8.45 (br s, 1H), 7.88 (d, 7.4 Hz, 1H), 7.61 (d, J=3.8 Hz, 2H), 7.58–7.44 (m, 1H), 2.76 (dt, $J_1$=13.8 Hz, $J_2$=6.0 Hz, 2H), 2.57–2.44 (m, 2H), 2.35–2.28 (m, 2H), 1.97–1.89 (m, 2H).

Examples for the Preparation of Intermediates III

EXAMPLE 9

4-(4-Cyano-3-fluoro-phenyl)-piperazine-1-carboxylic Acid tert-Butyl Ester 2,4-Difluorobenzonitrile (5.00 g, 35.94 mmol), tert-butyl-1-piperazinecarboxylate (6.69 g, 35.92 mmol) and potassium carbonate (10.0 g, 72.4 mmol) were combined in dimethylsulfoxide (40 mL) and stirred at 150° C. overnight. The reaction mixture was cooled to ambient temperature, poured into water (150 mL) and extracted into ethyl acetate (150 mL). The extract was washed twice with water and once with brine, dried over magnesium sulfate and concentrated. The residue was purified by flash chromatography (2"×5" silica gel). The column was flushed with 500 mL each 10% and 20% ethyl acetate/hexane and the product removed with an additional 500 mL of 20% ethyl acetate/hexane. Concentration gave 4-(4-cyano-3-fluoro-phenyl)-piperazine-1-carboxylic acid tert-butyl ester as a white solid (3.28 g, 30%) which had mp 130.5–131.0° C.

$^1H$ NMR $CDCl_3$ δ 7.42 (t, J=8.2 Hz, 1H), 6.63 (dd, $J_1$=8.9 Hz, $J_2$=2.4 Hz, 1H), 6.55 (dd, $J_1$=12.67 Hz, $J_2$=2.3 HZ, 1H), 3.59 (t, J=5.3 Hz, 4H), 3.34 (t, J=5.3 Hz, 4H), 1.49 (s, 9H).

EXAMPLE 10

2-Fluoro-4-piperazin-1-yl-benzonitrile

A solution of 4-(4-cyano-3-fluoro-phenyl)-piperazine-1-carboxylic acid tert-butyl ester (6.97 g, 22.83 mmol) in methanol (250 mL) was saturated with HCl gas and stirred at ambient temperature overnight. The reaction was concentrated, saturated sodium bicarbonate (250 mL) was added and the slurry was stirred for 1 hour. The resulting solid was filtered off, rinsed well with water, air dried then evacuated overnight. As water was removed from the solid, it turned to a milky yellow solid which slowly solidified to give 2-fluoro-4-piperazin-1-yl-benzonitrile as a waxy solid (3.84 g, 82%).

mp 67–68° C. $^1$H NMR CDCl$_3$ δ 7.33 (dd, J$_1$=8.8 Hz, J$_2$=7.8 Hz, 1H), 6.58 (dd, J$_1$=8.9 Hz, J$_2$=2.4 Hz, 1H), 6.49 (dd, J$_1$=13.1 Hz, J$_2$=2.4 Hz, 1H), 3.27–3.23 (m, 4H), 2.97–2.93 (m, 4H), 1.70 (s, 1H). $^{13}$C NMR CDCl$_3$ δ 166.46, 163.09, 155.67, 155.53, 133.81, 133.78, 115.41, 109.77, 109.75, 100.63, 100.31, 88.15, 87.80, 47.98, 45.59. Analysis calculated for C$_{11}$H$_{12}$FN$_3$: C, 64.37; H, 5.89; N, 20.47. Found: C, 64.33; H, 5.82: N, 20.35.

Preparation of Compounds With General Formula IV

EXAMPLE 11

1-(4-Fluoro-phenyl)-4-cyclohexanone

A solution of 1-(1,4-dioxa-spiro[4.5]dec-8-yl)-4-(4-fluoro-phenyl)-piperazine (3.13 gm) (C$_{18}$H$_{25}$FN$_2$O$_2$) in 100 ml 3N hydrochloric acid and 100 ml dioxane was stirred at ambient temperature for 2 hours. The mixture is cooled to 0° C., neutralized with 2N sodium hydroxide and extracted with 2×100 ml ethyl acetate. The ethyl acetate layer was washed with water and brine (each 2×40 ml), dried over sodium sulfate and concentrated to a solid. This material, which was recrystallized from ethyl ether (1.5 gm), has a melting point of 104–106° C.

Elemental analysis of a sample of this material (C$_{16}$H$_{21}$FN$_{20}$): C, 69.61%, H, 7.9%, N, 10.3%.

Example for the Preparation of Intermediate VIII

EXAMPLE 12

2-Fluoro-4-(4-3'H-spiro[cyclohex-1,1'-isobenzofuran]-4-yl-piperazin-1-yl)-benzonitrile)

To a 100 ml 3-necked flask was added (2.01 g, 0.0107 mol) 2-bromobenzyl alcohol and 23 ml dry THF. The reaction mixture was cooled to −60° C. (dry ice/acetone bath). 2.0 Equivalents of n-butyl lithium (8.60 ml) were added in 0.5 ml increments over approximately 30 minutes (min). The temperature was maintained below −40° C. during the addition. The dianion (lithium salt) began to precipitate after 15 min. The mixture was allowed to warm to −20° C. by removing the dry ice acetone bath. A thick white precipitate formed which is the dianion salt. After stirring approx. 1½ hours, the flask was again cooled to −60° C. 1,4 Cyclohexanedione ethylene ketal (1.68 g, 0.0107 mol) in 10 ml THF was added via an addition funnel. The temperature was kept below −40° C. When the addition was complete, the flask was allowed to slowly warm to room temperature and the reaction was stirred 18 hours at room temperature.

To quench the reaction, excess aqueous ammonium chloride was added. The THF was removed by rotary evaporation. 2 ml Ethyl acetate was added. The organic layer was washed with water and the water layer was back extracted. The organic extractions were combined and dried with MgSO$_4$. The organics were concentrated down, leaving a thick yellow oil. Hexane:ethyl acetate (1:1) was added and a precipitate began to form. The precipitate was filtered off and the procedure with the mother liquor. 2.23 g repeated to yield a white solid, 8-(2-Hydroxymethyl-phenyl)-1,4-dioxa-spiro[4.5]decan-8-ol, 80% yield.

Example for the Preparation of Compounds With General Structure IX

EXAMPLE 13

1-(1,4-Dioxa-spiro[4.5]dec-8-yl)-4-(4-fluoro-phenyl)-piperazine

A mixture of 11.5 gm of 1-(4-fluoro-phenyl)-piperazine 10.0 gm of 1,4-cyclohexanedione mono-ethylene ketal (available from Aldrich) and 27.2 gm NaB(OAc)$_3$ in 250 ml dichloroethylene was kept for 18 hours at ambient temperature. The solvents were removed and the residue partitioned between ethyl acetate (200 ml) and 2N NaOH (200 ml). The ethyl acetate layer is washed with 2×20 ml water and dried over Na$_2$SO$_4$. The crude 1-(1,4-dioxa-spiro[4.5]dec-8-yl)-4-(4-fluoro-phenyl)-piperazine (20.1 gm of a solid) obtained after removing the solvents had a melting point of 116–118° C. A sample of this material (C$_{18}$H$_{25}$FN$_2$O$_2$) showed an elemental analysis of C, 67.24%, H, 8.22%. N, 8.98%.

Example for Preparation of Compounds With General Structure X

EXAMPLE 14

1,7,10-Trioxa-dispiro[2.2.4.2]dodecane 12.00 g (76.83 mmol, 1.0 equiv.) of 1,4 Cyclohexanedione ethylene ketal was added to 120 ml methylene chloride along with 18.8 g (99.88 mmol, 1.3 equiv.) of trimethyl sulfonium methyl sulfate. 40 ml 50% sodium hydroxide (NaOH) was added last and the reaction was refluxed for 24 hours. The methylene chloride was removed, 200 ml ether was added and the ether layer was washed with water. The organic layer was dried with sodium sulfate and concentrated down, leaving a yellow oil, 1,7,10-trioxa-dispiro [2.2.4.2]dodecane. (12.13 g, 93% yield). No further purification was necessary.

GC-MS FW=170.21. 1 peak at 1.456 min. $^1$H NMR (250 MHz, CDCl$_3$) δ 0.4–1.8 (8H, m), 2.6 (2H, s), 3.9 (4H, s). $^{13}$C NMR (63 MHz, CDCl$_3$) δ 107.59, 63.98, 57.12, 53.31, 32.54, 30.12.

Example for the Preparation of Compounds With General Structure XII

EXAMPLE 15

8-(2-Bromo-phenoxymethyl-1,4-dioxa-spiro[4.5]decan-8-ol 11.98 g (70.38 mmol, 1.0 equiv.) of epoxide 1,7,10-Trioxa-dispiro[2.2.4.2]dodecane, was added to a 250 ml round-bottom flask containing 100 ml of toluene. 2-Bromo phenol (8.03 ml, 70.38 mmol, 1.0 equiv.) was then added via a syringe and the contents of the flask were stirred for 5 minutes. 5.69 ml (1.0 equiv.) Pyridine was then added and the reaction was refluxed 18 hours.

WORK-UP: Concentrate crude reaction mixture, add 200 ml ethyl acetate and wash with water, dry organic layer with sodium sulfate. Dark brown oil subjected to flash chrom. 20% ethyl acetate, Hex. (6.10 g, yellow oil, 25% yield).

GC-MS FW=343.42. 6.923 min. $^1$H NMR (250 MHz, CDCl$_3$) δ 1.6–1.8 (4H, m), 1.8–2.1 4H, m), 2.3 (1H, s), 3.85 (2H, s), 3.9–4.0 (4H, m), 6.8 (2H, m), 7.2 (1H, m), 7.5 (1H, m). $^{13}$C NMR (75 MHz, CDCl$_3$) δ 154.92, 133.21, 128.56, 122.33, 113.69, 112.48, 108.79, 76.74, 69.85, 64.32, 64.19, 31.74, 30.01.

Example for Preparation of Compounds With General Structure XIII

EXAMPLE 16

8-(2-Bromo-phenoxymethyl)-1,4-dioxa-spiro[4.5] dec-7-ene 8-(2-Bromo-phenoxymethyl)-1,4-dioxa-spiro[4.5]decan-8-ol, (42.6498 g, 7.72 mmol, 1.0 equiv.) was added to a dry 3-necked flask with 15 ml CH$_2$Cl$_2$ and (4.03 ml, 3.0 equiv.) of diisopropylethylamine. The reaction was then cooled to −12° C. and 2.02 g (1.5 equiv.) of methane sulfonic acid in 15 ml CH$_2$Cl$_2$ was added dropwise. The reaction was allowed to warm to room temperature. After 1 hour, 25 ml water and 25 ml CH$_2$Cl$_2$ were added. The organic layer was dried with sodium sulfate and concentrated, leaving a yellow oil. Flash chromatography 10% EtOAc, hexane) gave 0.7569 g oil of an 8-(2-bromo-phenoxymethyl)-1,4-dioxa-spiro[4.5]dec-7-ene, 30% yield.

GC-MS FW=325.20. 1 peak at 6.4556 min. $^1$H NMR (250 MHz, CDCl$_3$) δ 1.83 (2H, t), 2.40 (4H, m), 3.98 (4H, s), 4.47 (2H, s), 5.77 (1H, br singlet), 6.81–6.89 (2H, m), 7.19–7.25 (1H, m), 7.50–7.54 (1H, m). $^{13}$C NMR (63 MHz, CDCl$_3$) δ 24.79, 30.76, 35.45, 64.38, 72.27, 107.84, 112.29, 113.58, 121.84, 122.34, 128.36, 132.86, 133.23, 155.04.

Example for Preparation of Compounds With General Structure XVII

EXAMPLE 17

Spiro-[(cyclohexan-1,3'-isoindolin)-1'-one]-4-one

A solution of 2-bromobenzonitrile (2.00 g, 10.99 mmol) in tetrahydrofuran (50 mL) was cooled to −78° C. and n-butyllithium (2.5M, 4.6 mL, 11.5 mmol) was added slowly. The resulting orange-brown solution was stirred for 10 min., then a solution of 1,4-cyclohexanedione mono-ethylene ketal (1.70 g, 10.88 mmol) in tetrahydrofuran (25 mL) was added dropwise over 5 minutes. The reaction was stirred an additional 15 min, quenched with water (25 mL) and immediately extracted into chloroform (100 mL). This extract was dried over magnesium sulfate and concentrated to give the crude spiroimidate as a waxy yellow solid (2.74 g, 97%).

Mp 178–179° C.$^{41}$. $^1$H NMR CDCl$_3$ δ 7.81 (d, J=7.4 Hz, 1H), 7.54 (dt, J$_1$=7.3 Hz, J$_2$=1.1 Hz, 1H), 7.45 (dt, J$_1$=7.4 Hz, J$_2$=1.0 Hz, 1H), 7.33 (d, J=7.4 Hz, 1H), 4.05–3.98 (m, 2H), 2.45–2.05 (m, 4H), 1.79 (br d, J=10.0 Hz, 4H). Analysis calculated for C$_{15}$H$_{17}$NO$_3$; C, 69.46; H, 6.61; N, 5.40. Found: C, 69.33; H, 6.62; N, 5.01.

Additional Examples for Preparing Compounds With General Structure XVII

EXAMPLE 18

3'H-Spiro[cyclohexane-1,1'-benzofuran]-4-one Diethylacetal 0.7112 g (2.19 mmol, 1.0 equiv.) of 8-(2-Bromo-phenoxymethyl)-1,4-dioxa-spiro[4.5]dec-7-ene, was added to toluene, 40 ml, along with (2.0 equiv., 1.18 ml, 4.38 mmol) of tributyltin hydride. AIBN (13 mol %) was then added and the reaction was refluxed for 3 hours. Ethyl acetate (EtOAc) (15 ml) and 3.0 ml aqueous potassium fluoride were added. The reaction was stirred overnight and a white precipitate was filtered off. The EtOAc layer was washed with water and the organic layer was dried with sodium sulfate. Flash chromatography (10% EtOAc, hexane) yielded a white solid.

GC-MS FW=246.31. 1 peak at 4.950 min. $^1$H NMR (250 MHz, CDCl$_3$) δ 1.56–2.15 (8H, m), 3.9 (4H, s), 4.4 (2H, s), 6.8–6.9 (2H, m), 7.1–7.2 (2H, m). $^{13}$C NMR (63 MHz, CDCl$_3$) δ 159.32, 134.98, 128.28, 122.96, 120.50, 109.71, 107.90, 80.50, 64.34, 45.23, 34.02, 32.04.

Examples for the Preparation of Compounds With General Structure III Wherein PG=Tertiary Butoxy Carbonyl

EXAMPLE 19 trans-4-3'H-Spiro[cyclohex-1,1'-isobenzofuran]-4-yl-piperazine-1-carboxylic Acid tert-Butyl Ester Maleate tert-Butyl 1-piperazinecarboxylate (0.86 g, 4.62 mmol), 3'H-spiro[cyclohexane-1,1'-isobenzofuran]-4-one (0.93 g, 4.60 mmol) and sodium triacetoxyborohydride (1.96 g, 9.25 mmol) were stirred in 1,2-dichloroethane (50 mL) overnight at ambient temperature. The reaction was concentrated and stirred 1 hour with 25 mL each 1N sodium hydroxide and ethyl acetate. The organic phase was washed with brine, dried over magnesium sulfate and concentrated to a thick colorless oil (1.74 g). The crude product was loaded onto a silica gel column (1.5"×4") and flushed with 20% ethyl acetate/hexane (250 mL). An additional 250 mL 20% ethyl acetate/hexane and 250 mL 30% ethyl acetate/hexane gave, after concentration, trans-4-3'H-spiro[cyclohex-1,1'-isobenzofuran]-4-yl-piperazine-1-carboxylic acid tert-butyl ester as a white solid (0.56 g, 33%). A portion of this was converted to the maleate salt in diethyl ether with 1 equiv. of maleic acid.

Mp 168–169° C. Analysis calculated for C$_{22}$H$_{32}$N$_2$O$_3$.C$_4$H$_4$O$_4$: C, 63.92; H, 7.43; N, 5.73. Found: C, 63.60; H, 7.03; N, 5.84.

Preparation of Compounds With General Structure Intermediates XX

EXAMPLE 20 trans-1-3'H-Spiro[cyclohex-1,1'-isobenzofuran]-4-yl-piperazine Dihydrochloride

HCl gas was bubbled through a solution of trans-3'H-spiro[cyclohex-1,1'-isobenzofuran]-4-yl-piperazine-1-carboxylic acid tert-butyl ester (0.52 g, 1.40 mmol) in ethyl ether (100 mL) for 3 min. Methanol (25 mL) was added to dissolve precipitated solids and the reaction was stirred at ambient temperature for 4 days. Filtered off the precipitate and air dried to yield 0.45 g (94%) of trans 1-3'H-Spiro [cyclohex-1,1'-isobenzofuran]-4-yl-piperazine dihydrochloride as a white solid.

Mp>260° C. Analysis calculated for C$_{17}$H$_{24}$N$_2$O.2HCl.0.5H$_2$O: C, 57.63; H, 7.68; N, 7.91. Found: C, 58.01; H, 7.73; N, 7.95.

Using Methods Scheme 1 and Scheme 3, the Following Compounds With General Formula I Were Prepared

EXAMPLE 21 trans-4-[4-(4-Fluoro-phenyl)-piperazin-1-yl]-spiro [cyclohexane-1-1'-isobenzofuran]-3'-one Maleate mp=194–195° C. Analysis calculated for C$_{23}$H$_{25}$FN$_2$O$_2$.C$_4$H$_4$O$_4$: C, 65.31; H, 5.89; N, 5.64. Found: C, 65.09; H, 6.00; N, 5.55.

EXAMPLE 22 trans, 1-(4-Fluoro-phenyl)-4-3'H-spiro[cyclohex-1-1'-isobenzofuran]4-yl-piperazine Mesylate mp>260° C. Analysis calculated for C$_{23}$H$_{27}$FN$_2$O.CH$_4$O$_3$S: C, 62.32; H, 6.75; N, 6.06. Found: C, 62.05: H, 7.01; N, 5.94.

EXAMPLE 23 trans, 1-(4-Fluoro-phenyl)-4-(5',6',7'-trifluoro-3'H-spiro[cyclohex-1,1'-isobenzofuran]-4-yl)-piperazine Dihydrochloride mp=256–258° C. Analysis calculated for C$_{23}$H$_{24}$F$_4$N$_2$O.2HC.0.75H$_2$O: C, 54.50; H, 5.46; N, 5.52. Found: C, 54.27; H, 5.43; N, 5.44.

EXAMPLE 24 trans, 1-(5'-Chloro-3'H-spiro[cyclohex-1,1'-isobenzofuran]-4-yl)-4-(4-fluoro-phenyl)-piperazine Dihydrochloride mp>260° C. Analysis calculated for $C_{23}H_{26}ClFN_2O.2HCl.0.25H_2O$: C, 57.75; H, 6.00; N, 5.86. Found: C, 57.71; H, 6.03; N, 5.81.

EXAMPLE 25 trans, 1-(4-Fluoro-phenyl)-4-(4'-trifluoromethyl-3'H-spiro[cyclohex-1,1'-isobenzofuran]-4-yl)-piperazine Dihydrochloride mp>260° C. Analysis calculated for $C_{24}H_{26}F_4N_2O.2HCl$: C, 56.81; H, 5.56; N, 5.52. Found: C, 56.64; H, 5.49; N, 5.66.

EXAMPLE 26 trans, 6'-Fluoro-4-[4-(4-fluoro-phenyl)-piperazin-1-yl]-spiro[cyclohexane-1,1'-isobenzofuran]-3'-one $C_{23}H_{24}F_2N_2O_2$, FW=398.45, 434.92 HCl. GC-MS 8.8 Min., M+398. mp>250° C. $^1$H NMR (CDCl$_3$, 250 MHz) d 1.60–1.65 (m, 2H), 2.0–2.1 (m, 4H), 2.3–2.4 (m, 2H), 2.5 (m, 1H), 2.7 (m, 4H), 3.2 (m, 4H), 6.8–7.0 (m, 4H), 7.1–7.2 (m, 2H), 7.9 (m, 1H). $^{13}$C NMR (CDCl$_3$, 63 MHz) d 24.50, 31.46, 50.05, 50.45, 57.31, 86.5, 108.59, 108.97, 115.30, 115.65, 116.96, 117.34, 177.55, 117.67, 128.13, 128.29, 159.01.

EXAMPLE 27 trans, 1-(2-Chloro-phenyl)-4-3'H-spiro[cyclohex-1,1'-isobenzofuran]-4-yl-piperazine Dihydrochloride mp>260° C. Analysis calculated for $C_{23}H_{27}ClN_2O.2HCl.H_2O$: C, 58.30; H, 6.59; N, 5.91. Found: C, 58.16; H, 6.53; N, 5.82.

EXAMPLE 28 trans, 1-(2-Methoxy-phenyl)-4-3'H-spiro[cyclohex-1,1'-isobenzofuran]-4-yl-piperazine Dihydrochloride mp>260° C. Analysis calculated for $C_{24}H_{30}N_2O_2.2HCl$: C, 63.85; H, 7.14; N, 6.21. Found: C, 64.10; H, 6.84; N, 5.73.

EXAMPLE 29 trans, 1-(4'-Bromo-3'H-spiro[cyclohex-1,1'-isobenzofuran]-4-yl)-4-(4-fluoro-phenyl)-piperazine Dihydrochloride mp>260° C. Analysis calculated for $C_{23}H_{26}BrFN_2O.2HCl.0.5H_2O$: C, 52.39; H, 5.54; N, 5.31. Found: C, 52.55; H, 5.57; N, 5.51.

EXAMPLE 30 trans, 1-(4-Fluoro-phenyl)-4-(5'-fluoro-3'H-spiro[cyclohex-1,1'-isobenzofuran]-4-yl)-piperazine Dihydrochloride mp>260° C. Analysis calculated for $C_{23}H_{26}F_2N_2O.2HCl.H_2O$: C, 58.11; H, 6.36; N, 5.89. Found: C, 58.44; H, 6.64; N, 5.66.

EXAMPLE 31 trans, 4-[4-(4-Fluoro-phenyl)-piperazin-1-yl]-3'H-spiro[cyclohexane-1,1'-isobenzofuran]-4'-carbonitrile Dihydrochloride mp>260° C. Analysis calculated for $C_{24}H_{26}FN_3O.2HCl$: C, 62.07; H, 6.08; N, 9.05. Found: C, 62.00; H, 6.23; N, 8.52.

EXAMPLE 32 trans, 4-[4-(4-Fluoro-phenyl)-piperazin-1-yl]-3'H-spiro[cyclohexane-1,1'-isobenzofuran]-4'-carboxylic Acid Amide Dihydrochloride mp>260° C. Analysis calculated for $C_{24}H_{28}FN_3O_2.2HCl.1.5H_2O$: C, 56.58; H, 6.53; N, 8.24. Found: C, 56.15; H, 6.52; N, 7.89.

EXAMPLE 33 trans, 2-(4-3'H-Spiro[cyclohex-1,1'-isobenzofuran]-4-yl-piperazin-1-yl)-benzonitrile $C_{24}H_{27}N_3O$, FW=373.50 (FREEBASE), 409.95 HCl. GC-MS 9.3 Min., M$^+$ 373. mp>250° C. (HCl). $^{13}$C NMR (CDCl$_3$, 63 MHz) δ 24.70, 33.49, 49.82, 51.87, 59.50, 70.43, 86.73, 105.70, 118.46, 121.10, 121.41, 121.49, 126.96, 127.34, 133.74, 134.35, 139.25, 146.17, 155.68.

EXAMPLE 34 trans, 1-(2-Fluoro-phenyl)-4-3'H-spiro[cyclohex-1,1'-isobenzofuran]-4-yl-piperazine $C_{23}H_{27}FN_2O$, FW=366.48, 402.93 HCl. GC-MS 7.67 Min., M+ 366. mp>250° C. $^{13}$C NMR (CDCl$_3$, 75 MHz) δ 24.81, 33.47, 50.03, 50.99, 51.04, 59.54, 70.48, 86.86. 115.95, 116.23, 118.81, 118.85, 121.12, 121.46, 122.24, 122.34, 124.41, 124.45, 127.00. 127.36, 139.29, 140.21, 140.31, 146.30, 154.16, 157.42.

EXAMPLE 35 trans, 1-(2,4-Dimethyl-phenyl)-4-3'H-spiro[cyclohex-1,1'-isobenzofuran]-4-yl-piperazine $C_{25}H_{32}N_2O$, FW=376.55, HCl 413.00. GC-MS 8.37 Min., M$^+$ 376. mp>250° C.

EXAMPLE 36 trans, 5-Fluoro-2-(4-3'H-spiro[cyclohex-1,1'-isobenzofuran]-4-yl-piperazin-1-yl)-benzonitrile $C_{24}H_{26}FN_3O$, FW=391.49, 427.94 HCl. GC-MS 8.84 Min., M$^+$ 391. mp>250° C. $^{13}$C NMR (CDCl$_3$, 75 MHz) δ 24.75, 33.51, 49.87, 52.41, 59.50, 70.48, 77.32, 86.76, 107.17, 107.30, 117.12, 117.16, 120.24, 120.35, 120.55, 120.92, 121.16, 121.20, 121.42, 127.01, 127.23, 127.39, 127.49, 139.31, 146.23, 152.57, 152.61, 155.26, 158.48.

EXAMPLE 37 trans, 2-Fluoro-4-(4-3'H-spiro[cyclohex-1,1'-isobenzofuran]-4-yl-piperazin-1-yl)-benzonitrile mp HCl>250° C., mesylate 263° C. (decomposition). $^1$H NMR (CDCl$_3$, 400 MHz) δ 1.6 (m, 2H), 1.9 (m, 4H), 2.0 (m, 2H), 2.4 (s, 1H), 2.69 (m, 4H), 3.37 (m, 4H), 5.0 (s, 2H), 6.63 (m, 2H), 7.2 (m, 4H), 7.4 (m, 1H). $^{13}$C NMR (CDCl$_3$, 100 MHz) δ 24.7, 33.0, 47.3, 49.4, 58.9, 70.5, 86.7, 100.4, 100.6, 109.7, 115.4, 121.1, 121.2, 127.1, 127.4, 133.9, 139.2, 146.2, 155.2, 155.3, 166.1. Analysis calculated for $C_{24}H_{26}FN_3O$ HCl: C, 67.36; H, 6.36; N, 9.82. Found: C, 67.04: H, 6.48; N, 9.94.

EXAMPLE 38 trans, 1-(2-Ethoxy-phenyl)-4-3'H-spiro[cyclohex-1,1'-isobenzofuran]-4-yl-piperazine $C_{25}H_{32}N_2O_2$, FW=392.54, 428.99 HCl. GC-MS 8.59 Min., M$^+$ 392. mp>250° C. $^{13}$C NMR (CDCl$_3$, 75 MHz) d 14.98, 24.90, 33.61, 50.24, 51.00, 59.83, 63.57, 70.48. 86.91, 112.51, 118.07, 121.02, 121.10, 121.56, 122.61, 124.11 127.23, 127.34, 139.30. 141.53, 146.33, 151.62.

EXAMPLE 39 trans, 1-(4-Fluoro-phenyl)-4-(4'-fluoro-3'H-spiro [cyclohex-1,1'-isobenzofuran]-4-yl)-piperazine Dihydrochloride mp>260° C. Analysis calculated for $C_{23}H_{26}F_2N_2O.2HCl.3H_2O$: C, 54.01; H, 6.70; N, 5.48. Found: C, 54.05; H, 6.70; N, 5.48.

EXAMPLE 40 trans, 4-[4-(2-Cyano-4-fluoro-phenyl)-piperazin-1-yl]-3'H-spiro[cyclohexane-1,1'-isobenzofuran]-4'-carbonitrile Hydrochloride mp>260° C. Analysis calculated for $C_{25}H_{25}FN_4O.HCl$: C, 66.29; H, 5.79; N, 12.37. Found: C, 65.85; H, 5.96; N, 12.26.

EXAMPLE 41 trans, 2-[4-(4'-Cyano-3'H-spiro[cyclohex-1,1'-isobenzofuran]-4-yl)-piperazin-1-yl]-5-fluoro-benzamide Dihydrochloride mp>260° C. $^{13}$C NMR DMSO $d_6$ δ 11.03 (br s, 1H), 8.30–8.27 (m, 2H), 7.80 (d, J=7.3 Hz, 1H), 7.69 (br s, 1H), 7.52 (t, J=7.7 Hz, 1H), 7.46 (dd, $J_1$=9.4 HZ, $J_2$=3.1 Hz, 1H), 7.38–7.31 (m, 1H), 7.30–7.24 (m, 1H), 5.17 (s, 2H), 3.78 (br d, J=10.2 Hz, 2H), 3.50–3.35 (m, 3H), 3.30–3.15 (m, 4H), 2.40–2.27 (m, 2H), 2.25–2.14 (m, 4H), 1.73–1.67 (m, 2H).

EXAMPLE 42 trans, 4-(4-3'H-Spiro[cyclohex-1,1'-isobenzofuran] yl-piperazin-1-yl)-benzonitrile $C_{24}H_{27}N_3O$, FW=373.50, 409.96 HCl. GC-MS 10.51 Min., M$^+$ 373. mp>250° C. $^{13}$C NMR (CDCl$_3$, 63 MHz) δ 24.71, 31.82, 33.06, 35.27, 47.44, 49.54, 58.99, 70.46. 70.69, 86.70, 100.0, 113.97, 120.11, 121.11, 121.26, 127.01, 127.18, 127.39, 133.41, 139.14, 146.14, 153.38.

EXAMPLE 43 trans, 1-(4'-Chloro-3'H-spiro[cyclohex-1,1'-isobenzofuran]-4-yl)-4-(4-fluoro-phenyl)-piperazine Dihydrochloride mp>260° C. Analysis calculated for $C_{23}H_{26}ClFN_2O.2HCl$: C, 58.30; H, 5.96; N, 5.91. Found: C, 58.52; H, 5.95; N, 5.61.

EXAMPLE 44 trans, 4-[4-(4-Cyano-phenyl)-piperazin-1-yl]-3'H-spiro[cyclohexane-1,1'-isobenzofuran]-4-carbonitrile Hydrochloride mp>260° C.

EXAMPLE 45 trans, 1-(4-Methoxy-phenyl)-4-3'H-spiro[cyclohex-1,1'-isobenzofuran]-4-yl-piperazine Dihydrochloride mp>260° C. Analysis calculated for $C_{24}H_{30}N_2O_2.2HCl$: C, 63.85; H, 7.14; N, 6.21. Found: C, 63.74; H, 7.07; N, 5.90.

EXAMPLE 46 trans, 1-(4-Chloro-phenyl)-4-3'H-spiro[cyclohex-1, 1'-isobenzofuran]-4-yl-piperazine Dihydrochloride mp>260° C. Analysis calculated for $C_{23}H_{27}ClN_2O.2HCl$: C, 60.60; H, 6.41; N, 6.15. Found: C, 60.22; H, 6.24; N, 6.03.

EXAMPLE 47 trans, 1-(4-Nitro-phenyl)-4-3'H-spiro[cyclohex-1-1'-isobenzofuran]-4-yl-piperazine Hydrochloride mp>260° C. Analysis calculated for $C_{23}H_{27}N_3O_3.HCl.0.25H_2O$: C, 63.59; H, 6.61; N, 9.67. Found: C, 63.52; H, 6.75; N, 9.48.

EXAMPLE 48 trans, 2-Fluoro-4-(4-3'H-spiro[cyclohex-1,1'-isobenzofuran]-4-yl-piperazin-1-yl)-benzamide $C_{24}H_{28}FN_3O_2$, FW=409.51, 445.97 HCl. MS M+1=410. mp>250° C. HCl. $^{13}$C NMR (CDCl$_3$, 75 MHz) δ 24.70, 33.07, 47.59, 49.49, 70.45, 86.72, 100.01, 100.48, 110.00, 121.10, 121.26, 127.0, 127.37, 133.06, 133.12, 139.14, 146.13, 155.25, 164.80. 165.27.

EXAMPLE 49 trans, 1-(3-Chloro-phenyl)-4-3'H-spiro[cyclohex-1, 1'-isobenzofuran]-4-yl-piperazine $C_{23}H_{27}ClN_2O$, FW=382.94, 419.40 HCl. GC-MS 9.16 Min., M$^+$ 382. mp>250° C. HCl. $^{13}$C NMR (DMSO-d$_6$, 75 MHz) δ 22.26, 33.24, 44.59, 48.72, 62.06, 69.89, 85.04, 114.09, 115.20, 119.17, 121.20, 122.48, 127.04, 127.56, 130.68, 134.00, 139.06, 145.04, 150.91.

EXAMPLE 50 trans, 1-3'H-Spiro[cyclohex-1,1'-isobenzofuran]-4-yl-4-m-tolyl-piperazine $C_{24}H_{30}N_2O$, FW=362.52, 398.98 HCl. GC-MS 8.50 Min., M$^+$ 362. mp>250° C. HCl. $^{13}$C NMR (CDCl$_3$, 62 MHz) δ 21.89, 24.87, 33.30, 49.62, 50.08, 59.30, 70.51, 77.43, 86.86, 113.12, 116.79, 120.52, 121.13, 121.44, 127.07, 127.38, 128.97, 138.67, 139.24, 146.35, 151.51.

EXAMPLE 51 trans, 2-(4-3'H-Spiro[cyclohex-1,1'-isobenzofuran]-4-piperazin-1-yl)-benzamide $C_{24}H_{29}N_3O_2$, FW=391.52, 427.98 HCl. $^{13}$C NMR (CDCl$_3$, 63 MHz) δ 24.71, 33.14, 50.58, 53.71, 59.30, 70.46, 120.19, 121.09, 121.32, 124.59, 127.00, 127.38, 131.72, 132.46, 139.15, 168.60.

EXAMPLE 52 trans, 4-(4-3'H-Spiro[cyclohex-1-1'-isobenzofuran]-4-yl-piperazin-1-yl)-phenylamine Dihydrochloride mp>260° C.

EXAMPLE 53 trans, N-[4-(4-3'H-Spiro[cyclohex-1,1'-isobenzofuran]-4-yl-piperazin-1-yl)-phenyl]-acetamide Dihydrochloride mp>260° C. Analysis calculated for $C_{25}H_{231}N_3O_2.2HCl.0.5H_2O$: C, 61.60; H, 7.03; N, 8.61. Found: C, 61.80; H, 7.03; N, 8.41.

EXAMPLE 54 trans, 6-(4-3'H-Spiro[cyclohex-1,1'-isobenzofuran]-4-yl-piperazin-1-yl)-nictinonitrile Dihydrochloride mp>260° C. Analysis calculated for $C_{23}H_{26}N_4O.2HCl.1.5H_2O$: C, 58.23; H, 6.59; N, 11.81. Found: C, 58.22; H, 6.54; N, 11.56.

EXAMPLE 55 cis, 1-(3,4-Dichloro-phenyl)-4-3'H-spiro[cyclohex-1,1'-isobenzofuran]-4-yl-piperazine $C_{23}H_{26}Cl_2N_2O$, FW=417.38, 453.84 HCl. GC-MS 10.44 Min., (M−1) 416. mp>250° C. HCl. $^1$H NMR (DMSO-d$_6$, 400 MHz, HCl) δ 1.6 (m, 2H), 2.1 (m, 5H), 3.0–3.1 (m, 2H), 3.4 (m, 4H), 3.6–3.9 (m, 4H), 4.9 (s, 2H), 6.9–7.0 (m, 1H), 7.2–7.25 (m, 4H), 7.4 (m, 1H), 7.8 (m, 1H).

EXAMPLE 56 trans, 2-Fluoro-4-[4-(5'-fluoro-3'H-spiro[cyclohex-1,1'-isobenzofuran]-4-yl)-piperazin-1-yl]-benzonitrile Hydrochloride mp>260° C. Analysis calculated for $C_{24}H_{25}F_2N_3O.HCl$: C, 64.64; H, 5.88; N, 9.42. Found: C, 64.50; H, 6.07; N, 9.49.

EXAMPLE 57 trans, 1-3'H-Spiro[cyclohex-1,1'-isobenzofuran]-4-yl-4-(3-trifluoromethyl-phenyl)-piperazine $C_{24}H_{27}F_3N_2O$, FW=416.49, 452.95 HCl. GC-MS 7.83 Min., M$^+$ 416. $^{13}$C NMR (CDCl$_3$, 100 MHz) δ 24.80, 33.18, 49.03, 49.81, 59.18, 70.51, 86.81, 111.95, 111.99, 115.67, 118.60, 121.12, 121.38, 127.06, 127.41, 129.51, 131.54, 139.20, 146.24, 151.46.

EXAMPLE 58 trans, 4-Fluoro-2-(4-3'H-spiro[cyclohex-1,1'-isobenzofuran]-4-yl-piperazin-1-yl)-benzonitrile $C_{24}H_{26}FN_3O$, FW=391.49, 427.94 HCl. GC-MS 9.02 Min., M$^+$ 391. $^1$H NMR (DMSO-d$_6$, 250 MHz, HCl) δ 1.6–1.7 (m, 2H), 2.1–2.2 (m, 7H), 3.1–3.9 (m, 8H), 5.0 (s, 1H), 7.1 (m, 1H), 7.2–7.3 (m, 6H), 7.9 (m, 2H).

EXAMPLE 59 trans, 1-3'H-Spiro[cyclohex-1-1'-isobenzofuran]-4-yl-4-(4-trifluoromethyl-phenyl)-piperazine Hydrochloride mp>260° C. Analysis calculated for $C_{24}H_{27}F_3N_2O.HCl.0.25H_2O$: C, 63.02; H, 6.28; N, 6.12. Found: C, 62.90; H, 6.28; N, 6.01.

EXAMPLE 60 trans, 1-(4-Methanesulfonyl-phenyl)-4-3'-spiro[cyclohex-1,1'-isobenzofuran]-4-yl-piperazine Hydrochloride mp>260° C. Analysis calculated for $C_{24}H_{30}N_2O_3S.HCl$: C, 62.25; H, 6.75; N, 6.05. Found: C, 61.99; H, 6.70; N, 5.91.

EXAMPLE 61 trans, (4-3'H-Spiro[cyclohex-1,1'-isobenzofuran]-4-yl-piperazin-1-yl)-benzamide $C_{24}H_{29}N_3O_2$, FW=391.52, 427.98 HCl MS (M+1) 392. H NMR (DMSO d$_6$, 75 MHz) δ 22.16, 33.14, 44.05, 48.63, 61.99, 69.82, 84.98, 114.08, 121.11, 122.42, 124.63, 126.97, 127.49, 128.82, 128.92, 138.97, 144.99, 151.43, 167.46.

EXAMPLE 62 trans, 1-Phenyl-4-3'H-spiro[cyclohex-1-1'-isobenzofuran]-4-yl-piperazine Dihydrochloride mp>260° C. Analysis calculated for $C_{23}H_{28}N_2O.2HCl$: C, 65.55; H, 7.18; N, 6.65. Found: C, 65.49: H, 7.47; N, 6.58.

EXAMPLE 63 trans, 2-Fluoro-4-[4-(6'-fluoro-3'H-spiro[cyclohex-1,1'-isobenzofuran]-4-yl)-piperazin-1-yl]-benzonitrile Mesylate mp=149–155° C. Analysis calculated for $C_{24}H_{25}F_2N_3O.CH_4O_3S.1.5H_2O$: C, 56.38; H, 6.06; N, 7.89. Found: C, 56.91; H, 5.83; N, 7.50.

EXAMPLE 64 trans, 4-[4-(5'-Chloro-3'H-spiro[cyclohex-1,1'-isobenzofuran]-4-yl-piperazin-1-yl]-2-fluoro-benzamide Dihydrochloride mp>260° C. $^1$H NMR DMSO d$_6$ 11.07 (br s, 1H), 7.66 (t, J=8.8 Hz, 1H), 7.43–7.26 (m, 5H)), 6.91–6.86 (m, 2H), 4.98 (s, 2H), 4.03 (br d, J=12.8 Hz, 2H), 3.57–3.15 (m, 7H), 2.20–2.10 (m, 2H), 1.95–1.80 (m, 6H).

EXAMPLE 65 trans, 2-Fluoro-4-[4-(5-fluorospiro[benzofuran-3(2H),1'-cyclohexan]-4'-yl)-1-piperazinyl]-, Benzonitrite, Hydrochloride $C_{24}H_{25}F_2N_{3O}$, FW=409.48, 445.93 HCl. GC-MS 11.06 Min., M$^+$ 409. MP>250° C.

EXAMPLE 66 trans, 1-(4'-Bromo-3'H-spiro[cyclohex-1,1'-isobenzofuran]-4-yl)-4-m-tolyl-piperazine Dihydrochloride mp>260° C. Analysis calculated for $C_{25}H_{29}BrN_2O.2HCl$: C, 56.05; H, 6.08; N, 5.45. Found: C, 55.96; H, 5.95; N, 5.31.

Using the Methods Described in Scheme 1 and 5 the Title Compounds of Examples 67–69 Have Been Prepared

EXAMPLE 67 trans, 4-[4-(4-Fluorophenyl)-1-piperazinyl]-spiro[cyclohexane-1,1'-[1H]isoindol]-3'(2'H)-one Dihydrochloride mp=238.5–242° C. Analysis calculated for $C_{23}H_{26}.FN_3O.2HCl.2.5H_2O$: C, 55.54; H, 6.28; N, 8.44. Found: C, 55.49; H, 6.15; N, 8.24.

EXAMPLE 68 trans, 1-(3',3'-Dimethyl-3'H-spiro[cyclohex-1,1'-isobenzofuran]-4-yl)-4-(4-fluoro-phenyl)-piperazine Dihydrochloride mp>260° C. Analysis calculated for $C_{25}H_{31}FN_2O.2HCl.0.25H_2O$: C, 63.62; H, 7.15; N, 5.94. Found: C, 63.50; H, 6.92; N, 5.59.

EXAMPLE 69 trans, 1-[4-Fluorophenyl)-4-spiro[benzofuran-3(2H), 1'-cyclohexan]-4'-yl)-piperizine, Hydrochloride MP>250° C. (HCl). $^1$H NMR (250 MHz, CDCl$_3$) δ 1.5–1.8 (2H, br. m), 1.6–2.0 (6H, br. m), 2.45 (1H, m), 2.7 (4H, m), 3.1 (4H, m), 6.8–7.4 (8H, aromatic). $^{13}$C NMR (63 MHz, CDCl3) δ 24.93, 34.17, 45.11, 49.55, 50.53, 61.11, 83.34, 109.91, 115.29, 115.64, 117.63, 117.75, 120.16, 124.60, 128.19, 135.06, 148.01, 159.87.

EXAMPLE 70 trans, 2-Fluoro-4-[4-spiro[benzofuran-3(2H),1'-cyclohexan]-4'-yl]-1-piperazinyl]-benzonitrile Hydrochloride $C_{24}H_{26}FN_3O$ (freebase), FW=391.49, 427.95 (HCl). GC-MS 11.22 Min., M$^+$ 391. MP>250° C. $^1$H NMR (CDCl$_3$, 250 MHz) d 1.5–1.6 (m, 2H), 1.9–2.1 (m, 6H), 3.1–3.2 (m, 2H), 3.2–3.3 (m, 3H), 3.8 (m, 2H), 4.1–4.2 (m, 3H), 6.9–7.0 (m, 2H), 7.0 (m, 1H), 7.2–7.3 (m, 2H), 7.7 (m, 2H).

EXAMPLE 71 trans, 4-[4-(5,6-Difluorospiro[benzofuran-3(2H),1'-cyclohexan]-4'-yl)-1-piperazinyl]-2-fluoro-benzonitrile Hydrochloride $C_{24}H_{24}F_3N_3O$, FW=427.47, 463.93 HCl. GC-MS 11.38 Min., M$^+$ 427. $^{13}$C NMR (DMSO-d$_6$, 75 MHz, HCl) δ 22.11, 32.76, 43.49, 44.05, 47.94, 62.48, 83.26, 87.43, 87.64, 99.15, 99.44, 100.99, 101.31, 110.73, 114.00, 114.28, 115.14, 129.94, 134.25, 154.12, 154.27, 162.57, 165.89 (some fluoride splitting not seen in this $^{13}$C NMR).

EXAMPLE 72 trans, 4-(4-Spiro[benzofuran-3(2H),1'-cyclohexan]-4'-yl-1-piperazinyl)-benzonitrile Hydrochloride $C_{24}H_{27}N_3O$, FW=373.50, 409.96 HCl. GC-MS 11.03 Min., M$^+$ 373. $^{13}$C NMR (DMSO-d$_6$, 75 MHz) δ 22.38, 33.62, 43.54, 43.96, 48.09, 63.23, 82.5, 100.0, 109.84, 114.83, 120.17, 128.44, 133.53, 151.0, 159.0.

EXAMPLE 73 trans-4-Fluoro-2(4-3'H-spiro[cyclohex-1,1'-isobenzofuran]-4-yl-piperazine-1-yl)benzonitrile Hydrochloride mp=>250° C. FW=391.49 (freebase), GC-MS, $t_R$=8.89 min., M$^+$=391. $^1$H NMR (CDCl$_3$, 300 MHz) δ 1.5–1.6 (m, 2H), 1.8–2.1 (m, 6H), 2.45 (s, 1H), 2.7 (br. s., 4H), 3.3 (br. s., 4H), 5.1 (s, 2H), 6.6–6.7 (m, 2H), 7.1–7.3 (m, 5H), 7.55–7.60 (m, 1H). $^{13}$C NMR (CDCl$_3$, 75 MHz) δ 24.70, 33.36, 49.73, 51.53, 59.40, 70.75, 77.42, 86.71, 101.03, 101.07, 105.85, 106.16, 108.59, 108.90, 117.99, 121.16, 121.40, 126.67, 127.05, 127.40, 136.34, 136.48, 139.27, 146.22, 157.90, 158.03, 164.31, 167.69.

EXAMPLE 74 trans-2-Fluoro-4-[4-(5-fluorospiro[benzofuran-3(2H),1'-cyclohexan]-4'-yl)-1-piperazinyl]-benzonitrile Hydrochloride mp=>250° C. FW=409.48 (freebase), GC-MS, $t_R$=11.058 min., M$^+$=409.

EXAMPLE 75 trans-1-(4'-Bromo-3'H-spiro[cyclohex-1,1'-isobenzofuran]-4-yl)-4-m-tolyl-piperazine Dihydrochloride mp>260° C. Analysis calculated for $C_{24}H_{29}BrN_2O.2HCl$: C, 56.05; H, 6.08; N, 5.45. Found: C, 55.96; H, 5.95; N, 5.31.

EXAMPLE 76 trans-2-[4-(3',3'-Dimethyl-3'H-spiro[cyclohex-1,1'-isobenzofuran]-4-yl)-piperazin-1-yl]-5-fluoro-pyrimidine Mesylate FW=396.51 (freebase), GC-MS, $t_R$=7.457 min., M$^+$=396. $^1$H NMR (CDCl$_3$, 300 MHz) δ 1.5 (s, 6H), 1.6–1.7 (m, 2H), 1.8–2.1 (m, 6H), 2.4–2.5 (m, 1H), 2.6 (m, 4H), 3.8 (m, 4H), 7.1–7.2 (m, 1H), 7.25–7.4 (m, 3H), 8.2 (s, 2H). $^{13}$C NMR (CDCl$_3$, 75 MHz) δ 24.75, 31.06, 36.43, 44.82, 49.67, 60.11, 83.46, 85.12, 120.93, 121.71, 127.09, 127.66, 144.95, 145.23, 145.35, 147.07, 149.92, 153.21, 158.97.

EXAMPLE 77 cis-4-[4-(4-Fluorophenyl)-1-piperazinyl]-2',3'-dihydro-spiro[cyclohexane-1,1'-[1H]inden]-3'-ol Maleate mp 200–201.5° C. Analysis calculated for $C_{24}H_{29}FN_2O.0.75C_4H_4O_4.0.75H_2O$: C, 67.41; H, 7.02; N, 5.82. Found: C, 67.24; H, 6.71; N, 5.66.

EXAMPLE 78 cis-4-[4-(4-Fluorophenyl)-1-piperazinyl]-spiro[cyclohexane-1,1'-[1H]inden]-3'(2'H)-one, O-Methyloxime, Dihydrochloride mp>260° C. Analysis calculated for $C_{25}H_{30}FN_3O.2HCl.0.50H_2O$: C, 61.35; H, 6.80; N, 8.59. Found: C, 61.51; H, 6.96; N, 8.57.

EXAMPLE 79 cis-4-[4-(4-Fluorophenyl)-1-piperazinyl]-spiro[cyclohexane-1,1'-[1H]inden]-3'(2'H)-one Dihydrochloride mp>260° C. Analysis calculated for $C_{24}H_{27}FN_2O.2HCl.0.50H_2O$: C, 62.61; H, 6.57; N, 6.08. Found: C, 62.66; H, 6.38; N, 6.17.

EXAMPLE 80

1-(1,4-Dioxa-spiro[4.5]dec-8-yl)-4-(4-fluoro-phenyl)-piperazine mp 116–118° C. Analysis calculated for $C_{18}H_{25}FN_2O_2$: C, 67.48; H, 7.86; N, 8.74. Found: C, 67.24; H, 8.22; N, 8.98.

EXAMPLE 81 cis-1-(4-Fluorophenyl)-4-spiro[cyclohexane-1,1'-[1H]inden]4-yl-piperazine Maleate mp 231–233.5° C. Analysis calculated for $C_{24}H_{27}FN_2.C_4H_4O_4.0.25H_2O$: C, 69.62; H, 6.57; N, 5.80. Found: C, 69.77; H, 6.43; N, 5.72.

EXAMPLE 82 cis-1-(2',3'-Dihydrospiro[cyclohexane-1,1'-[1H]inden]-4-yl)-4-(4-fluorophenyl)-piperazine Dihydrochloride mp>260° C. Analysis calculated for $C_{24}H_{29}FN_2.2HCl$: C, 65.90; H, 7.14; N, 6.40. Found: C, 65.63; H, 7.04; N, 6.29.

EXAMPLE 83 cis-4-[4-(2',3'-Dihydro-3'-hydroxyspiro[cyclohexane-1,1'-[1H]inden]-4-yl)-1-piperazinyl]-2-fluoro-benzonitrile Maleate mp 204–205° C. Analysis calculated for $C_{25}H_{28}FN_3O \cdot C_4H_4O_4 \cdot 0.25H_2O$: C, 66.21; H, 6.23; N, 7.99. Found: C, 66.27; H, 6.24; N, 7.88.

EXAMPLE 84 cis-4-[Spiro[cyclohexane-1,1'-[1H]inden]-3'(2'H)-one]-1-piperazinyl-2-fluoro-benzonitrile Hydrochloride mp>260° C. Analysis calculated for $C_{25}H_{26}FN_3O \cdot HCl \cdot 0.25H_2O$: C, 67.56; H, 6.24; N, 9.45. Found: C, 67.52; H, 6.44; N, 9.38.

EXAMPLE 85 trans-1-[4-(1,1-Dioxidospiro[benzo[b]thiophene-3(2H),1'-cyclohex]-4'-yl)]-4-(4-fluorophenyl)-piperazine Maleate mp 214.5–215.5° C. Analysis calculated for $C_{23}H_{27}FN_2O_2S \cdot C_4H_4O_4$: C, 61.12; H, 5.89; N, 5.28. Found: C, 60.88; H, 5.88; N, 4.69.

EXAMPLE 86 trans-4-[4-(1,1-Dioxidospiro[benzo[b]thiophene-3(2H),1'-cyclohex]-4'-yl)-1-piperazinyl]-2-fluoro-benzonitrile Maleate mp 140–143° C. Analysis calculated for $C_{24}H_{26}FN_3O_2S \cdot 0.25C_4H_4O_4 \cdot 0.25H_2O$: C, 60.04; H, 5.49; N, 7.50. Found: C, 59.73; H, 5.94; N, 5.79.

EXAMPLE 87 cis-4-[4-(2',3'-Dihydro-3'-hydroxyspiro[cyclohexane-1,1'-[1H]inden]-4-yl)-1-piperazinyl]-2-fluoro-benzonitrile Maleate (−Enantiomer)

mp 206–207° C. Analysis calculated for $C_{25}H_{28}FN_3O \cdot C_4H_4O_4$: C, 66.78; H, 6.18; N, 8.06. Found; C, 66.48; H, 6.03; N, 7.98. $[\alpha]_D = -10.22$, c=0.450 (MeOH).

EXAMPLE 88 cis-4-[4-(2',3'-Dihydro-3'-hydroxyspiro[cyclohexane-1,1'-[1H]inden]-4-yl)-1-piperazinyl]-2-fluoro-benzonitrile Maleate (+Enantiomer)

mp 199–199.5° C. Analysis calculated for $C_{25}H_{28}FN_3O \cdot C_4H_4O_4 \cdot 0.50H_2O$: C, 65.48; H, 6.26; N, 7.92. Found: C, 65.48; H, 6.20; N, 7.80. $[\alpha]_D = +9.48$, c=0.485 (MeOH).

EXAMPLE 89 trans-4-[4-(4-Fluoro-phenyl)-piperazin-1-yl]-1-(4-pyrrolidin-1-ylmethyl-phenyl)-cyclohexanol Dimaleate mp 150.5–152° C. Analysis calculated for $C_{27}H_{36}FN_3O \cdot 2C_4H_4O_4 \cdot 0.50H_2O$: C, 61.94; H, 6.68; N, 6.19. Found: C, 61.67; H, 6.70; N, 6.36.

EXAMPLE 90 cis-4-[4-(Spiro[cyclohexane-1,1'-[1H]inden]-4-yl)-1-piperazinyl]-2-fluoro-benzonitrile Maleate mp 218.5–219.5° C. Analysis calculated for $C_{25}H_{26}FN_3 \cdot C_4H_4O_4$: C, 69.17; H, 6.00; N, 8.34. Found: C, 68.99; H, 6.02; N, 7.94.

EXAMPLE 91 trans-4-[4-(4'-Bromo-3'H-spiro[cyclohex-1,1'-isobenzofuran]-4-yl)-piperazine-1-yl]-2-fluoro-benzonitrile mp=>250° C. $^1$H NMR (CDCl$_3$, 400 MHz) δ 1.57–1.66 (m, 3H), 1.85–2.15 (m, 5H), 2.37 (s, 1H), 2.65–2.68 (m, 4H), 3.34–3.37 (m, 4H), 5.00 (s, 2H), 6.53–6.57 (m, 2H), 7.10–7.16 (m, 2H), 7.36–7.41 (m, 2H).

EXAMPLE 92 cis-N-[4-[4-(4-Cyano-3-fluorophenyl)-1-piperazinyl]-2',3'-dihydrospiro[cyclohexane-1,1'-[1H]inden]-3'-yl]-acetamide Mesylate (+Enantiomer)

mp=>250° C. FW=446.57 (freebase), API-MS, (M+1)=447. $^1$H NMR (CDCl$_3$, 400 MHz) δ 1.35–1.45 (m, 3H), 1.51–1.59 (m, 6H), 1.98 (s, 3H), 2.12 (s, 1H), 2.34 (br. s., 1H), 2.52–2.55 (m, 1H), 2.67 (br. s, 4H), 3.35 (br. s., 4H), 5.41–5.47 (m, 1H), 5.97–5.99 (m, 1H), 6.5–6.6 (m, 2H), 7.19–7.35 (m, 5H).

EXAMPLE 93 cis-N-[4-[4-(4-Cyano-3-fluorophenyl)-1-piperazinyl]-2',3'-dihydrospiro[cyclohexane-1,1'-[1H]inden]-3'-yl]-acetamide Mesylate (−Enantiomer)

mp=>250° C. FW=446.57 (freebase), API-MS (M−1)=445.

EXAMPLE 94 cis-4-[4-Phenyl-1-piperazinyl]-spiro[cyclohexane-1,1'-[1H]inden]-3'(2'H)-one Mesylate mp=>250° C. FW=360.50 (freebase), GC-MS $t_R$=9.043 min., M+=360. $^1$H NMR (CDCl$_3$, 400 MHz) δ 1.31–1.34 (m, 2H), 1.57–1.70 (m, 2H), 2.04–2.14 (m, 4H), 2.36 (s, 1H), 2.61 (s, 2H), 2.71 (s, 4H), 3.25 (s, 4H), 6.83–6.87 (m, 1H), 6.94–6.96 (m, 2H), 7.24–7.38 (m, 4H), 7.68 (m, 2H), 7.7 (m, 1H).

EXAMPLE 95 trans-3-(4-3'H-Spiro[cyclohex-1,1'-isobenzofuran]-4-yl-piperazin-1-yl)-benzonitrile Hydrochloride mp=>250° C. FW=373.50 (freebase), $t_R$=9.39 min., GC-MS, M$^+$=373. $^1$H NMR (CDCl$_3$, 400 MHz) δ 1.64–1.76 (m, 2H), 1.94–1.94 (br. s, 4H), 2.02–2.06 (m, 2H), 2.41 (s, 1H), 2.73 (br. s, 4H), 3.27 (br. s., 4H), 5.07 (s, 2H), 7.09 7.14 (m, 3H), 7.26–7.35 (m, 5H). $^{13}$C NMR (CDCl$_3$, 75 Mhz) δ 24.79, 33.14, 48.69, 49.70, 59.09, 70.51, 86.77, 112.99, 118.21, 119.44, 119.67, 121.13, 121.32, 122.34, 127.04, 127.40, 129.84, 139.22, 146.24. 151.38.

EXAMPLE 96 trans-1-(3-Methoxy-phenyl)-4-3'H-spiro[cyclohex-1,1'-isobenzofuran]-4-yl-piperazine Hydrochloride mp=>250° C. FW=378.52 (freebase), $t_R$=8.83 min., M+=378. $^1$H NMR (CDCl$_3$, 400 MHz) δ 1.63–1.66 (m, 2H), 1.93–2.1 (m, 6H), 2.2 (br. s, 1H), 2.72 (br. s., 4H), 3.24 (br. s., 4H), 3.8 (s, 3H), 5.05 (s, 2H), 6.40–6.57 (m, 3H), 7.12–7.35 (m, 5H). $^{13}$C NMR (CDCl$_3$, 100 MHz) δ 24.66, 33.27, 49.22, 49.88, 55.10, 59.51, 70.42, 86.69, 102.34, 104.34, 108.70, 121.01, 121.43, 126.99, 127.30, 129.70, 139.11, 152.60, 160.51.

EXAMPLE 97 trans-5-Chloro-2-(4-3'H-spiro[cyclohex-1,1'-isobenzofuran]-4-yl-piperazin-1-yl)-pyrimidine Maleate mp 229.5–230° C. Analysis calculated for $C_{21}H_{25}ClN_4O \cdot C_4H_4O_4$: C, 59.94; H, 5.83; N, 11.18. Found: C, 59.79; H, 5.79; N, 11.28.

What is claimed is:

1. A compound of the formula

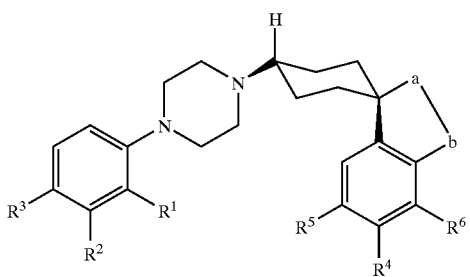

wherein a is oxygen, $CH_2$, $C(CH_3)_2$, $NR^{10}$, sulfur, SO or $SO_2$;

b is oxygen, $CH_2$, C=O, C=$NR^{11}$, C=NOH, $SO_2$, Sulfur, SO, C=NO($C_1$–$C_5$)alkyl or $CR^7R^8$;

each of $R^1$ through $R^8$ is selected, independently, from hydrogen, halo, trifluoromethyl, cyano and hydroxy, or $R^7$ and $R^8$ together can be C(=O)$NH_2$ or C(=O)N($C_1$–$C_4$)alkyl, with the proviso that neither $R^7$ nor $R^8$ can be halo when a is oxygen, $NR^{11}$, sulfur, SO or $SO_2$; and each of $R^{10}$ and $R^{11}$ is selected, independently, from hydrogen, benzyl and ($C_1$–$C_6$)alkyl;

and the pharmaceutically acceptable salts of such compounds.

2. A compound according to claim 1, wherein a is oxygen.

3. A compound according to claim 2, wherein b is $CH_2$.

4. A compound according to claim 3, wherein $R^4$, $R^5$ and $R^6$ are hydrogen.

5. A compound according to claim 4, wherein $R^3$ is selected from chloro, cyano and fluoro.

6. A compound according to claim 5, wherein $R^2$ is selected from chloro, cyano and fluoro.

7. A pharmaceutical composition for treating or preventing a condition selected from psychosis, nonorganic psychosis, personality disorders, schizophrenic and schizoaffective disorders, bipolar disorders, dysphoric mania, Parkinson's disease, extrapyramidal side effects from neuroleptic agents, neuroleptic malignant syndrome, tardive dyskinesia, and nausea, emesis, hyperthermia and amenorrhea in a mammal, comprising an amount of a compound according to claim 1 that is effective in treating or preventing such a condition, and a pharmaceutical acceptable carrier.

8. A method of treating a condition selected from psychosis, nonorganic psychosis, personality disorders, schizophrenic and schizoaffective disorders, bipolar disorders, dysphoric mania, and Parkinson's disease, in a mammal, comprising administering to said mammal an amount of a compound according to claim 1 that is effective in treating such condition.

* * * * *